United States Patent
Alberati-Giani et al.

(10) Patent No.: US 7,176,316 B2
(45) Date of Patent: Feb. 13, 2007

(54) AMINO-PIPERIDINE DERIVATIVES

(75) Inventors: Daniela Alberati-Giani, Zofingen (CH); Simona Maria Ceccarelli, Basel (CH); Emmanuel Pinard, Linsdorf (FR); Henri Stadler, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 70 days.

(21) Appl. No.: 10/778,560

(22) Filed: Feb. 13, 2004

(65) Prior Publication Data

US 2004/0167166 A1 Aug. 26, 2004

(30) Foreign Application Priority Data

Feb. 17, 2003 (EP) ................... 03003526

(51) Int. Cl.
*C07D 211/56* (2006.01)
(52) U.S. Cl. ................... 546/193; 546/223
(58) Field of Classification Search ........... 546/223, 546/193, 207, 192, 187; 514/329, 317
See application file for complete search history.

(56) References Cited

U.S. PATENT DOCUMENTS

| 4,145,427 A * | 3/1979 | Langbein et al. ........... 514/329 |
| 6,911,458 B2 * | 6/2005 | Eriksson et al. ........... 514/329 |

FOREIGN PATENT DOCUMENTS

| WO | WO 99/45011 A1 | 9/1999 |
| WO | WO 01/81308 A2 | 11/2001 |
| WO | WO 03/013527 A1 | 2/2003 |

OTHER PUBLICATIONS

Lewis, D. A., et al., J. A. Neuron vol. 28, pp. 325-334 (2000).
Vandenberg, R. J., et al., Exp. Opin. Ther. Targets, vol. 5(4), pp. 507-518 (2001).
Nakazato, A. et al., Exp. Opin. Ther. Patents vol. 10(1) pp. 75-98 (2000).
Sharma, T., Br. J. Psychiatry, vol. 174 (Suppl. 38) pp. 44-51 (1999).
Javitt, D. C., et al., Biol. Psychiatry, vol. 45, pp. 668-679 (1999).
Mohn, A. R., et al., Cell, vol. 98, pp. 427-436 (1999).
Bliss, T. V. P. et al., Nature, vol. 361, pp. 31-39 (1993).
Tang, J. P. et al., Nature, vol. 401, pp. 63-69 (1999).
Gainetdinov , R. R., et al., Trends in Pharm. Sci. vol. 23(8) pp. 367-373 (2002).
Lopez-Corcuera, B., et al., Mol. Mem. Biol. vol. 18, pp. 13-20 (2001).
Bergeron, R. et al., Proc. Natl. Acad. Sci. USA vol. 95, pp. 15730-15734 (1998).
Armer, R. E. et al., Exp. Opin. Ther. Patents vol. 11(4), pp. 563-572 (2001).
Pralong, E, et al., Prog. Neurobiol. vol. 67, pp. 173-202 (2002).
Carlsson, M. L., J. Neural Trans. vol. 105, pp. 525-535 (1998).

* cited by examiner

*Primary Examiner*—Thomas McKenzie
*Assistant Examiner*—Raymond Covington
(74) *Attorney, Agent, or Firm*—George W. Johnston; Patricia S. Rocha-Tramaloni; Kimberly J. Prior

(57) ABSTRACT

The present invention relates to compounds of the general formula

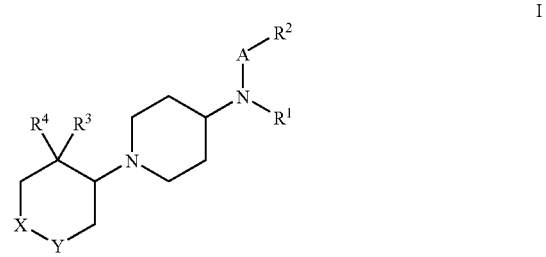

wherein
X and Y are each independently selected from —CH$_2$— or —O—, with the proviso that X and Y are not simultaneously —O—; A is —S(O)$_2$— or —C(O)—; and R$^1$, R$^2$, R$^3$, and R$^4$ are as defined in the specification. The compounds are GlyT-1 inhibitors and are useful for the treatment of psychoses, pain, dysfunction in memory and learning, schizophrenia, dementia and other diseases in which cognitive processes are impaired, such as attention deficit disorders or Alzheimer's disease.

28 Claims, No Drawings

AMINO-PIPERIDINE DERIVATIVES

FIELD OF THE INVENTION

The present invention relates to amino substituted piperidines, to the inhibition of glycine transporter 1 (GlyT-1), and to the treatment of schizophrenia and other CNS diseases.

BACKGROUND OF THE INVENTION

Schizophrenia is a progressive and devastating neurological disease characterized by episodic positive symptoms such as delusions, hallucinations, thought disorders and psychosis and persistent negative symptoms such as flattened affect, impaired attention and social withdrawal, and cognitive impairments (Lewis D A and Lieberman J A, Neuron, 28:325–33, 2000). For decades research has focused on the "dopaminergic hyperactivity" hypothesis which have led to therapeutic interventions involving blockade of the dopaminergic system (Vandenberg R J and Aubrey K R., Exp. Opin. Ther. Targets, 5(4): 507–518, 2001; Nakazato A and Okuyama S, et al., Exp. Opin. Ther. Patents, 10(1): 75–98, 2000). This pharmacological approach poorly address negative and cognitive symptoms which are the best predictors of functional outcome (Sharma T., Br. J. Psychiatry, 174(suppl. 28): 44–51, 1999).

A complementary model of schizophrenia was proposed in the mid-1960' based upon the psychotomimetic action caused by the blockade of the glutamate system by compounds like phencyclidine (PCP) and related agents (ketamine) which are non-competitive NMDA receptor antagonists. Interestingly in healthy volunteers, PCP-induced psychotomimetic action incorporates positive and negative symptoms as well as cognitive dysfunction, thus closely resembling schizophrenia in patients (Javitt D C et al., Biol. Psychiatry, 45: 668–679, 1999). Furthermore transgenic mice expressing reduced levels of the NMDAR1 subunit displays behavioral abnormalities similar to those observed in pharmacologically induced models of schizophrenia, supporting a model in which reduced NMDA receptor activity results in schizophrenia-like behavior (Mohn A R et al., Cell, 98: 427–236, 1999).

Glutamate neurotransmission, in particular NMDA receptor activity, plays a critical role in synaptic plasticity, learning and memory, such as the NMDA receptors appears to serve as a graded switch for gating the threshold of synaptic plasticity and memory formation (Wiley, N Y; Bliss T V and Collingridge G L, Nature, 361: 31–39, 1993). Transgenic mice overexpressing the NMDA NR2B subunit exhibit enhanced synaptic plasticity and superior ability in learning and memory (Tang J P et al., Natur, 401–63–69, 1999).

Thus, if a glutamate deficit is implicate in the pathophysiology of schizophrenia, enhancing glutamate transmission, in particular via NMDA receptor activation, would be predicted to produce both anti-psychotic and cognitive enhancing effects.

The amino acid glycine is known to have at least two important functions in the CNS. It acts as an inhibitory amino acid, binding to strychnine sensitive glycine receptors, and it also influences excitatory activity, acting as an essential co-agonist with glutamate for N-methyl-D-aspartate (NMDA) receptor function. While glutamate is released in an activity-dependent manner from synaptic terminals, glycine is apparently present at a more constant level and seems to modulate/control the receptor for its response to glutamate.

One of the most effective ways to control synaptic concentrations of neurotransmitter is to influence their re-uptake at the synapses. Neurotransmitter transporters by removing neurotransmitters from the extracellular space, can control their extracellular lifetime and thereby modulate the magnitude of the synaptic transmission (Gainetdinov R R et al, Trends in Pharm. Sci., 23(8): 367–373, 2002).

Glycine transporters, which form part of the sodium and chloride family of neurotransmitter transporters, play an important role in the termination of post-synaptic glycinergic actions and maintenance of low extracellular glycine concentration by re-uptake of glycine into presynaptic nerve terminals and surrounding fine glial processes.

Two distinct glycine transporter genes have been cloned (GlyT-1 and GlyT-2) from mammalian brain, which give rise to two transporters with ~50% amino acid sequence homology. GlyT-1 presents four isoforms arising from alternative splicing and alternative promoter usage (1a, 1b, 1c and 1d). Only two of these isoforms have been found in rodent brain (GlyT-1a and GlyT-1b). GlyT-2 also presents some degree of heterogeneity. Two GlyT-2 isoforms (2a and 2b) have been identified in rodent brains. GlyT-1 is known to be located in CNS and in peripheral tissues, whereas GlyT-2 is specific to the CNS. GlyT-1 has a predominantly glial distribution and is found not only in areas corresponding to strychnine sensitive glycine receptors but also outside these areas, where it has been postulated to be involved in modulation of NMDA receptor function (Lopez-Corcuera B et al., Mol. Mem. Biol., 18:13–20, 2001). Thus, one strategy to enhance NMDA receptor activity is to elevate the glycine concentration in the local microenvironment of synaptic NMDA receptors by inhibition of GlyT-1 transporter (Bergereon R. Et al., Proc. Natl. Acad. Sci. USA, 95:15730–15734, 1998).

Glycine transporters inhibitors are suitable for the treatment of neurological and neuropsychiatric disorders. The majority of diseases states implicated are psychoses, schizophrenia (Armer R E and Miller D J, Exp. Opin. Ther. Patents, 11 (4): 563–572, 2001), psychotic mood disorders such as severe major depressive disorder, mood disorders associated with psychotic disorders such as acute mania or depression, associated with bipolar disorders and mood disorders, associated with schizophrenia, (Pralong E T et al., Prog. Neurobiol., 67:173–202, 2002), autistic disorders (Carlsson M L, J. Neural Trans,. 105: 525–535, 1998), cognitive disorders such as dementias, including age related dementia and senile dementia of the Alzheimer type, memory disorders in a mammal, including a human, attention deficit disorders and pain (Armer R E and Miller D J, Exp. Opin. Ther. Patents, 11 (4):563–572, 2001).

Thus, increasing activation of NMDA receptors via GlyT-1 inhibition may lead to agents that treat psychosis, schizophrenia, dementia and other diseases in which cognitive processes are impaired, such as attention deficit disorders or Alzheimer's disease.

SUMMARY OF THE INVENTION

It is an object of the present invention to provide compounds of formula I per se and pharmaceutically acceptable acid addition salts of formula I:

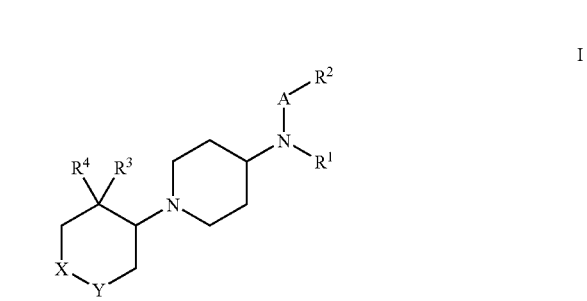

wherein
R¹ is lower alkyl, —(CH₂)ₙ-aryl, unsubstituted or substituted by one or two substituents selected from the group consisting of lower alkyl, lower alkoxy, —OCF₃, halogen, —NR'R" and trifluoromethyl, or is heteroaryl;
R² is lower alkyl, —(CH₂)ₙ-aryl, unsubstituted or substituted by one or two substituents selected from the group consisting of lower alkyl, lower alkoxy, halogen, trifluoromethyl, nitro, cyano, —NR'R", hydroxy, and a heteroaryl group, or is heteroaryl, unsubstituted or substituted by one or two substituents selected from the group consisting of lower alkyl and halogen;
R³ is heteroaryl or is aryl, unsubstituted or substituted by halogen or lower alkyl;
R⁴ is hydrogen or hydroxy;
A is —S(O)₂— or —C(O)—;
X and Y are each independently selected from the group consisting of —CH₂— and —O—, with the proviso that X and Y are not simultaneously —O—;
R' and R" are each independently selected from the group consisting of hydrogen, lower alkyl and —C(O)-lower alkyl;
n is 0, 1 or 2;

or a pharmaceutically acceptable acid addition salt thereof.

Furthermore, the invention includes all racemic mixtures, all their corresponding enantiomers and/or optical isomers.

It has surprisingly been found that these compounds are good inhibitors of the glycine transporter 1 (GlyT-1) and that they have a good selectivity to glycine transporter 2 (GlyT-2) inhibitors. Therefore, it is another object of the invention to provide pharmaceutical compositions containing a compound of the invention and a pharmaceutically acceptable carrier. It is a further option of the present invention to provide a method for the control or prevention of illnesses such as psychoses, dysfunction in memory and learning, schizophrenia, dementia and other diseases in which cognitive processes are impaired, such as attention deficit disorders or Alzheimer's disease which comprises administering to an individual a therapeutically effective amount of a compound of the invention. The preferred indications using the compounds of the present invention are the treatment of schizophrenia, cognitive impairment and Alzheimer's disease.

DETAILED DESCRIPTION OF THE INVENTION

The present invention relates to compounds of general formula I, to pharmaceutical composition containing them, and to their use in the treatment of neurological and neuropsychiatric disorders.

As used herein, the term "lower alkyl" denotes a saturated straight- or branched-chain alkyl group containing from 1 to 6 carbon atoms, for example, methyl, ethyl, propyl, isopropyl, n-butyl, 1-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues is as defined above, and which is attached via an oxygen atom.

The term "aryl" denotes a monovalent cyclic aromatic radical consisting of one or more fused rings, in which at least one ring is aromatic in nature, for example phenyl or naphthyl.

The term "heteroaryl" denotes a monovalent heterocyclic 5 or 6-membered aromatic radical, wherein the heteroatoms are selected from N, O or S, for example, the groups thiophenyl, pyridinyl, pyrimidinyl, imidazolyl, piperidinyl, furanyl, pyrrolyl, isoxazolyl, pyrazolyl, pyrazinyl, benzo[1.3]dioxolyl, benzo{b}thiophenyl or benzotriazolyl, "Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention relates to compounds of the formula

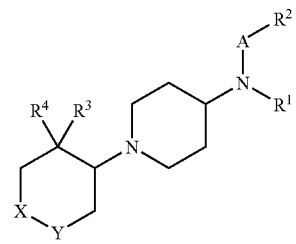

I wherein
R¹ is lower alkyl, —(CH₂)ₙ-aryl, unsubstituted or substituted by one or two substituents selected from the group consisting of lower alkyl, lower alkoxy, —OCF₃, halogen, —NR'R" and trifluoromethyl, or is heteroaryl;
R² is lower alkyl, —(CH₂)ₙ-aryl, unsubstituted or substituted by one or two substituents selected from the group consisting of lower alkyl, lower alkoxy, halogen, trifluoromethyl, nitro, cyano, —NR'R", hydroxy, and a heteroaryl group, or is heteroaryl, unsubstituted or substituted by one or two substituents selected from the group consisting of lower alkyl and halogen;
R³ is heteroaryl or is aryl, unsubstituted or substituted by halogen or lower alkyl;
R⁴ is hydrogen or hydroxy;
A is —S(O)₂— or —C(O)—;
X and Y are each independently selected from the group consisting of —CH₂— and —O—, with the proviso that X and Y are not simultaneously —O—;
R' and R" are each independently selected from the group consisting of hydrogen, lower alkyl and —C(O)-lower alkyl;
n is 0, 1 or 2;

or a pharmaceutically acceptable acid addition salt thereof.

The invention also includes all racemic mixtures, all their corresponding enantiomers and/or optical isomers.

Several specific embodiments of the invention are described below. It will be understood by one skilled in the art, that these are not the only embodiments encompassed by the invention. The invention includes any subgenus of compounds derived from any combination of the defined variables in Formula I, whether or not specifically exemplified in the specification.

Preferred are compounds of formula

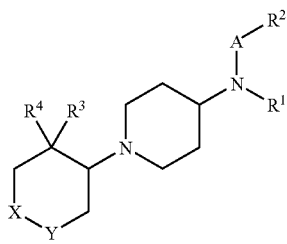

IA wherein

R¹ is lower alkyl, benzyl or is phenyl, unsubstituted or substituted by one or two substituents selected from the group consisting of lower alkyl, lower alkoxy, halogen and trifluoromethyl;

R² is lower alkyl, benzyl, thiophenyl or is phenyl, unsubstituted or substituted by one or two substituents selected from the group consisting of lower alkyl, lower alkoxy, halogen trifluoromethyl, nitro, amino, hydroxy and —NHC(O)-lower alkyl;

R³ is pyridin-3-yl, pyridin-4-yl or is phenyl, unsubstituted or substituted by halogen or lower alkyl;

R⁴ is hydrogen or hydroxy;

A is —S(O)₂— or —C(O)—;

X and Y are each independently selected from the group consisting of —CH₂— and —O—, with the proviso that X and Y are not simultaneously —O—;

or a pharmaceutically acceptable acid addition salt thereof.

Especially preferred compounds of the present application are those of formula I, wherein X and Y are both —CH₂—. For example, such compounds include those where A is —S(O)₂—. More specifically, the present invention includes compounds in which X and Y are both —CH₂—, A is —S(O)₂—, and R³ is a phenyl group, such as unsubstituted phenyl. For example, these compounds include those where X and Y are both —CH₂—, A is —S(O)₂—, and R³ is unsubstituted phenyl and R⁴ is hydrogen. The following compounds are encompassed by this embodiment:

(+/−)-3,4-dichloro-N-phenyl-N-[cis-1-(2-phenyl-cyclohexyl)-piperidin-4-yl]-benzenesulfonamide,
(+/−)-4-methoxy-N-(3-methoxy-phenyl)-N-[cis-1-(2-phenyl-cyclohexyl)-piperidin-4-yl]-benzenesulfonamide,
(+/−)-4-methoxy-N-phenyl-N-[cis-1-(2-phenyl-cyclohexyl)-piperidin-4-yl]-benzenesulfonamide,
(+/−)-N-(4-fluoro-phenyl)-4-methyl-N-[cis-1-(2-phenyl-cyclohexyl)-piperidin-4-yl]-benzenesulfonamide,
(+/−)-N-(4-fluoro-phenyl)-4-methoxy-N-[cis-1-(2-phenyl-cyclohexyl)-piperidin-4-yl]-benzenesulfonamide,
(+/−)-4-methoxy-N-[cis-1-(2-phenyl-cyclohexyl)-piperidin-4-yl]-N-(3-trifluoromethyl-phenyl)-benzenesulfonamide and
(+)-4-methoxy-N-phenyl-N-[cis-1-(2-phenyl-cyclohexyl)-piperidin-4-yl]-benzenesulfonamide.

Further preferred are compounds, wherein X and Y are both —CH₂—, and A is —C(O)—. Such compounds include those in which X and Y are both —CH₂—, A is —C(O)—, and R³ is a phenyl group, such as unsubstituted phenyl. For example, this embodiment includes compounds in which X and Y are both —CH₂—, A is —C(O)—, R³ is unsubstituted phenyl, and R⁴ is hydrogen. The following compounds are encompassed by this embodiment:

(+/−)-3-methoxy-N-[cis-1-(2-phenyl-cyclohexyl)-piperidin-4-yl]-N-p-tolyl-benzamide,
(+/−)-4-fluoro-N-[cis-1-(2-phenyl-cyclohexyl)-piperidin-4-yl]-N-p-tolyl-benzamide,
(+/−)-N-(4-chloro-phenyl)-N-[cis-1-(2-phenyl-cyclohexyl)-piperidin-4-yl]-3-trifluoromethyl-benzamide and
(+/−)-N-(4-chloro-phenyl)-3-methoxy-N-[cis-1-(2-phenyl-cyclohexyl)-piperidin-4-yl]-benzamide.

A further preferred group of compounds are those, wherein X and Y are both —CH₂—, A is —C(O)—, R³ is unsubstituted phenyl and R⁴ is hydroxy, for example the following compounds:

(+/−)-N-(4-fluoro-phenyl)-N-[cis-1-(2-hydroxy-2-phenyl-cyclohexyl)-piperidin-4-yl]-3-methoxy-benzamide,
(+/−)-N-(4-chloro-phenyl)-N-[cis-1-(2-hydroxy-2-phenyl-cyclohexyl)-piperidin-4-yl]-3-methoxy-benzamide,
(+/−)-4-fluoro-N-[cis-1-(2-hydroxy-2-phenyl-cyclohexyl)-piperidin-4-yl]-N-p-tolyl-benzamide,
(+/−)-N-[cis-1-(2-hydroxy-2-phenyl-cyclohexyl)-piperidin-4-yl]-N-(3-methoxy-phenyl)-benzamide and
(+/−)-N-[cis-1-(2-hydroxy-2-phenyl-cyclohexyl)-piperidin-4-yl]-3-methoxy-N-p-tolyl-benzamide.

Further preferred are compounds, wherein X and Y are both —CH₂—, A is —S(O)₂—, R³ is unsubstituted phenyl or phenyl, substituted by chloro, fluoro or methyl, and R⁴ is hydroxy, for example the following compounds:

(+/−)-N-[cis-1-(2-hydroxy-2-phenyl-cyclohexyl)-piperidin-4-yl]-4-methoxy-N-phenyl-benzenesulfonamide,
(+)-N-[cis-1-(2-hydroxy-2-phenyl-cyclohexyl)-piperidin-4-yl]-4-methoxy-N-phenyl-benzenesulfonamide,
(+/−)-N-(4-chloro-phenyl)-N-[cis-1-(2-hydroxy-2-phenyl-cyclohexyl)-piperidin-4-yl]-4-methoxy-benzenesulfonamide,
(+/−)-N-{cis-1-[2-(4-chloro-phenyl)-2-hydroxy-cyclohexyl]-piperidin-4-yl}-4-methoxy-N-phenyl-benzenesulfonamide,
(+/−)-N-{cis-1-[2-(4-fluoro-phenyl)-2-hydroxy-cyclohexyl]-piperidin-4-yl}-4-methoxy-N-phenyl-benzenesulfonamide,
(+/−)-N-[cis-1-(2-hydroxy-2-o-tolyl-cyclohexyl)-piperidin-4-yl]-4-methoxy-N-phenyl-benzenesulfonamide,
(+/−)-N-(4-fluoro-phenyl)-N-[cis-1-(2-hydroxy-2-phenyl-cyclohexyl)-piperidin-4-yl]-4-methoxy-benzenesulfonamide,
(+/−)-N-(4-fluoro-phenyl)-N-{cis-1-[2-(4-fluoro-phenyl)-2-hydroxy-cyclohexyl]-piperidin-4-yl}-4-methoxy-benzenesulfonamide,
(+/−)-N-[cis-1-(2-hydroxy-2-phenyl-cyclohexyl)-piperidin-4-yl]-4-methoxy-N-(3-methoxy-phenyl)-benzenesulfonamide,
(+/−)-N-{cis-1-[2-(4-fluoro-phenyl)-2-hydroxy-cyclohexyl]-piperidin-4-yl}-4-methoxy-N-(3-methoxy-phenyl)-benzenesulfonamide and
(+/−)-N-[trans-1-(2-hydroxy-2-phenyl-cyclohexyl)-piperidin-4-yl]-4-methoxy-N-phenyl-benzenesulfonamide.

Further preferred are compounds, wherein X and Y are both —CH₂—, A is —S(O)₂—, and R³ is pyridin-3-yl or pyridin-4-yl. Such compounds include those where X and Y are both —CH₂—, A is —S(O)₂—, and R³ is pyridin-3-yl or pyridin-4-yl, and R⁴ is hydroxy, for example the following compounds:

(+/−)-N-(4-chloro-phenyl)-N-[cis-1-(2-hydroxy-2-pyridin-3-yl-cyclohexyl)-piperidin-4-yl]-4-methoxy-benzenesulfonamide, (+/−)-N-[cis-1-(2-hydroxy-2-pyridin-4-yl-cyclohexyl)-piperidin-4-yl]-4-methoxy-N-phenyl-benzenesulfonamide, (+/−)-N-[cis-1-(2-hydroxy-2-pyridin-3-yl-cyclohexyl)-piperidin-4-yl]-4-methoxy-N-phenyl-benzenesulfonamide, (+/−)-N-(4-fluoro-phenyl)-N-[cis-1-(2-hydroxy-2-pyridin-4-yl-cyclohexyl)-piperidin-4-yl]-4-methoxy-benzenesulfonamide, (+/−)-N-[cis-1-(2-hydroxy-2-pyridin-4-yl-cyclohexyl)-piperidin-4-yl]-4-methoxy-N-(3-trifluoromethyl-phenyl)-benzenesulfonamide and (+/−)-N-[cis-1-(2-hydroxy-2-pyridin-3-yl-cyclohexyl)-piperidin-4-yl]-4-methoxy-N-(3-trifluoromethyl-phenyl)-benzenesulfonamide.

Further preferred are compounds, wherein X is —CH$_2$— and Y is —O—. For example compounds in which X is —CH$_2$—, Y is —O—, and A is —S(O)$_2$—. Such compounds include those where X is —CH$_2$—, Y is —O—, A is —S(O)$_2$— and R$^3$ is phenyl, such as unsubstituted phenyl. Example of such compounds are those in which X is —CH$_2$—, Y is —O—, and A is —S(O)$_2$—, R$^3$ is unsubstituted phenyl, and R$^4$ is hydroxy. The following is such a compound:

(+/−)-N-(4-fluoro-phenyl)-N-[cis-1-(4-hydroxy-4-phenyl-tetrahydro-pyran-3-yl)-piperidin-4-yl]-4-methoxy-benzenesulfonamide.

Further preferred are compounds, wherein X is —CH$_2$—, Y is —O— and A is —C(O)—. For example, compounds in which X is —CH$_2$—, Y is —O—, and A is —C(O)—, and R$^3$ is a phenyl group, such as unsubstituted phenyl. Such compounds include those where X is —CH$_2$—, Y is —O—, and A is —C(O)—, R$^3$ is unsubstituted phenyl, and R$^4$ is hydroxy, for example the following compound:

(+/−)-N-(4-fluoro-phenyl)-N-[cis-1-(4-hydroxy-4-phenyl-tetrahydro-pyran-3-yl)-piperidin-4-yl]-3-methoxy-benzamide.

Further preferred are those compounds wherein X and Y are both —CH$_2$—, A is —C(O)— and R$^3$ is heteroaryl, unsubstituted or substituted by halogen or lower alkyl or compounds wherein X and Y are both —CH$_2$—, A is —C(O)—, R$^2$ is heteroaryl, unsubstituted or substituted by one or two substituents selected from the group consisting of lower alkyl and halogen, and R$^4$ is hydrogen. One such heteroaryl group is a thiophenyl group.

Other embodiments of the present invention include those in which A is S(O)$_2$. For example compounds in which A is S(O)$_2$ and R$^1$ is a substituted or unsubstituted phenyl group. Other such compounds are those in which A is S(O)$_2$ and R$^2$ is a substituted or unsubstituted phenyl group.

Other embodiments of the present invention include those in which A is C(O). For example compounds in which A is C(O) and R$^1$ is a substituted or unsubstituted phenyl group. Other such compounds are those in which A is C(O) and R$^2$ is a substituted or unsubstituted phenyl group.

Still other embodiments of the present invention include those in which R$^3$ is an unsubstituted or substituted phenyl group. Also included are compounds in which R$^3$ is pyridine-3-yl or pyridine-4-yl.

The present compounds of formula I and their pharmaceutically acceptable salts can be prepared by methods known in the art, for example, by processes described below, which process comprises a) reacting a compound of formula

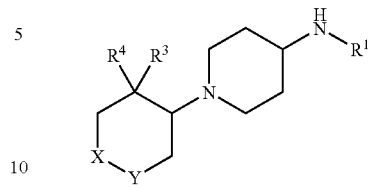

with a compound of formula

R$^2$SO$_2$Cl in the presence of a base and/or a proton scavenger to produce a compound of formula

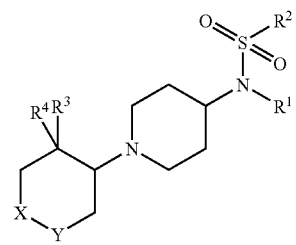

wherein X, Y, R$^1$, R$^2$ and R$^3$ are as defined above, or b) reacting a compound of formula

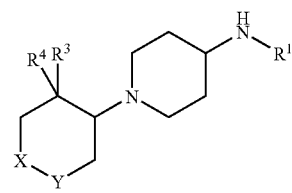

with a compound of formula

R$^2$COCl in the presence of a base and/or a proton scavenger to produce a compound of formula

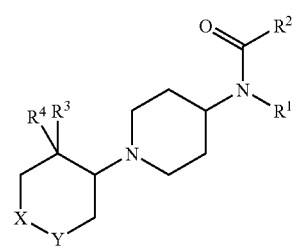

wherein X, Y, R$^1$, R$^2$ and R$^3$ are as defined above, or c) reacting a compound of formula

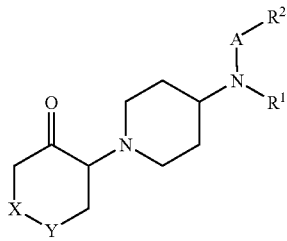

with a compound of formula

R³Li to produce a compound of formula

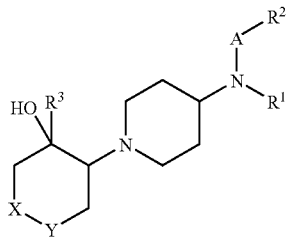

wherein A, X, Y, R¹, R² and R³ are as defined above, or
d) reacting a compound of formula

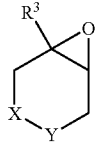

with a compound of formula

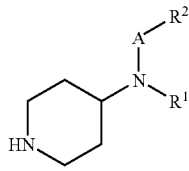

to produce a compound of formula

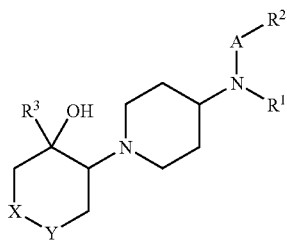

wherein A, X, Y, R¹, R² and R³ are as defined above, and
if desired, converting the compounds obtained into pharmaceutically acceptable acid addition salts.

The compounds of formula I can be prepared in accordance with process variant a) to d) and with the following schemes 1 to 7. All starting materials are commercially available or may be prepared according to methods well known in the art.

1. Preparation of Compounds of Formula I wherein R⁴ is Hydrogen (Scheme 1)

The compounds of the invention can be prepared by processes analogous to those established in the art.

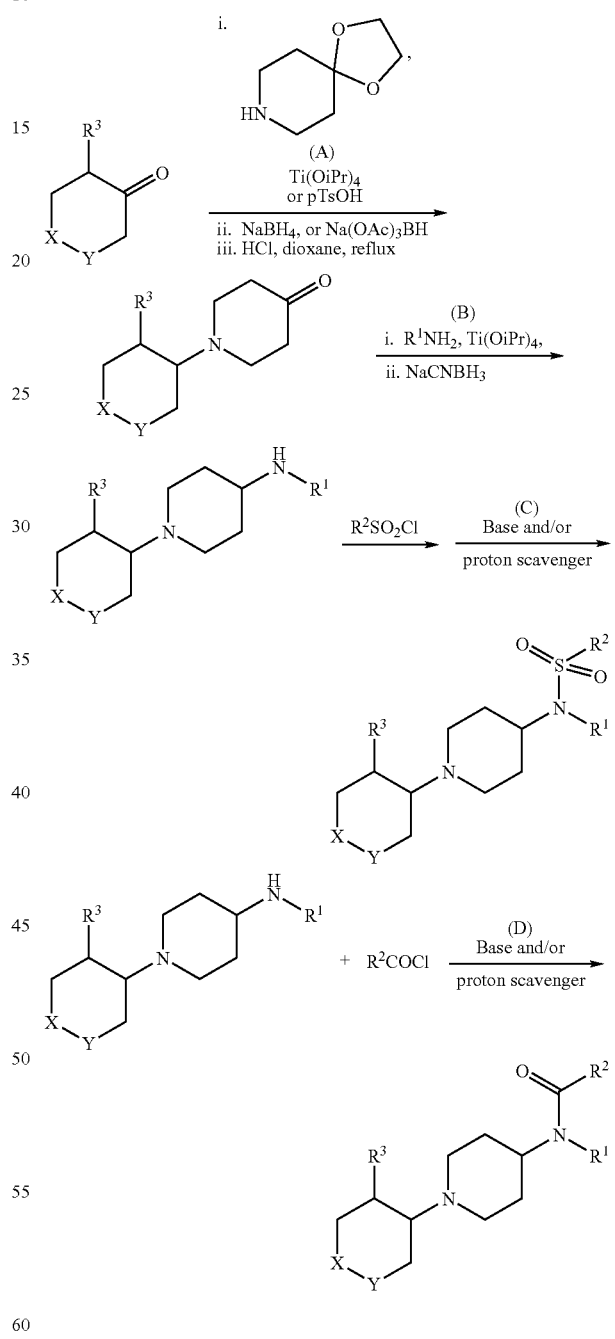

Compounds of formula I where R⁴ is hydrogen and A is an —S(O)₂— group are readily prepared by sulfonylation of the corresponding secondary amines using procedures established in the art, such as treating the amine with a sulfonyl chloride in the presence of a suitable base or proton scavenger (scheme 1, step C). Suitable amines include diisopropylethylamine, 4-dimethylaminopyridine, pyridine, 1,8-diazabicyclo[5.4.0]undec-7-ene and others. Proton scavengers include for example 1-methoxy-2-methyl-1-trimethylsilyloxy-propene.

Compounds of formula I where $R^4$ is hydrogen and A is a —C(O)— group are readily prepared by acylation of the corresponding secondary amines using procedures established in the art, such as treating the amine with an acyl chloride in the presence of a suitable base or proton scavenger (scheme 1, step D). Suitable amines include diisopropylethylamine, dimethylaminopyridine, triethylamine, etc. Proton scavengers include for example 1-methoxy-2-methyl-1-trimethylsilyloxy-propene.

The precursor secondary amines are prepared by reductive amination of a ketone, by reaction of the amine with the corresponding piperidone at 60° C. in ethanol in the presence of a stoichiometric quantity of titanium tetraisopropoxide, followed by reaction with sodium borohydride or sodium cyanoborohydride at room temperature (scheme 1, step B), or by reaction of the amine with the corresponding piperidone in the presence of an acid, as for example acetic acid, and sodium triacetoxyborohydride. Other reductive amination procedures established in the art can also be used.

The precursor ketone is prepared by reductive amination of the corresponding cycloalkanone with 1,4-dioxa-8-azaspiro[4.5]decane, followed by hydrolysis of the acetal in acidic conditions as shown in scheme 1, step A. Both titanium promoted or acid catalysed reductive amination is applicable. Only the cis arrangement is obtained. Deprotection of the acetal is obtained for example by treatment with concentrated chlorhydric acid in dioxane at the reflux temperature of the mixture.

Compounds of the invention can also be prepared by one of the above mentioned routes, using the methods and techniques of parallel solution phase synthesis.

2. Preparation of Compounds of Formula I wherein $R^4$ is Hydroxy (Schemes 2–6)

Scheme 2

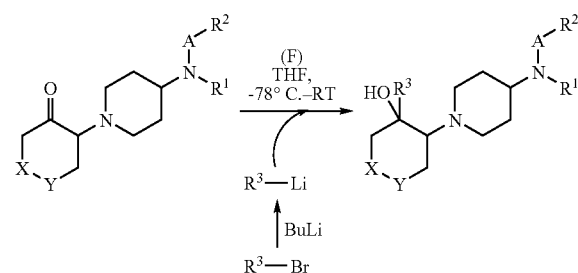

Compounds of formula I where $R^4$ is a hydroxy group and A is —S(O)$_2$— or —C(O)— can be prepared by reacting N-[1-(2-oxo-cycloalkyl)-piperidin-4-yl]-N-aryl-arylsulfonamides or N-[1-(2-oxo-cycloalkyl)-piperidin-4-yl]-N-aryl-arylamides at −78° C. in THF with one of the aryl lithium reagents $R^3$—Li, which are either commercially available or accessible from the corresponding aryl halides, according to procedures established in the art (scheme 2, step F). With this protocol only the cis arrangement is obtained.

Scheme 3

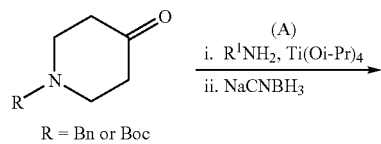

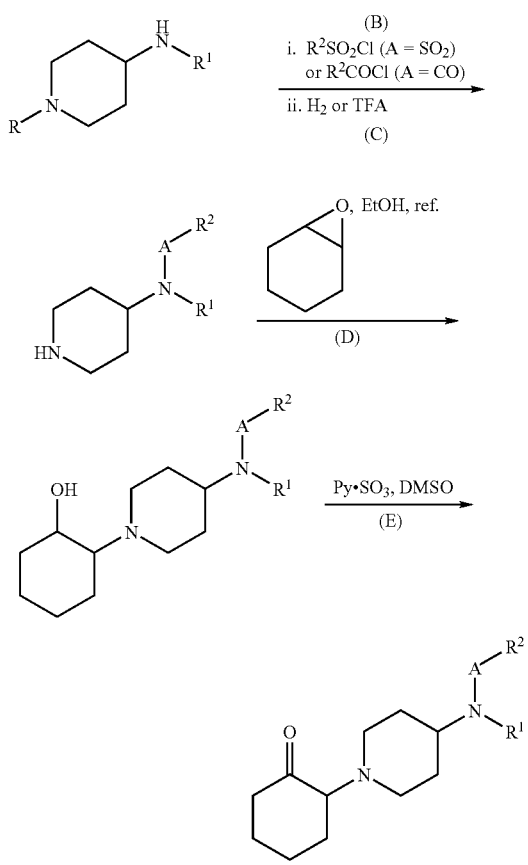

The precursor N-[1-(2-oxo-cycloalkyl)-piperidin-4-yl]-N-aryl-arylsulfonamides are obtained by oxidation of N-[1-(2-hydroxy-cycloalkyl)-piperidin-4-yl]-N-aryl-arylsulfonamides with one of the many procedures established in the art, for example with pyridine-sulfur trioxide complex in the presence of triethylamine and dimethylsulfoxide at room temperature. The same procedure applies for the synthesis of N-[1-(2-oxo-cycloalkyl)-piperidin-4-yl]-N-aryl-arylamides (scheme 3, step E).

The precursor cyclic secondary alcohol can be prepared by reaction of a suitably functionalized amine with a cyclic epoxide (scheme 3, step D), for example by mixing the amine and the epoxide in ethanol at the reflux temperature of the solvent.

A suitably functionalized amine can be accessed by reaction of N-tert-butoxycarbonyl-4-piperidone or N-benzyl-4-piperidinone with an amine $R^1NH_2$ (scheme 3, step A), followed by sulfonylation or acylation, as described above (scheme 3, step B). The protective group is then cleaved by acidic hydrolysis or hydrogenation according to procedures established in the art (scheme 3, step C).

Scheme 4

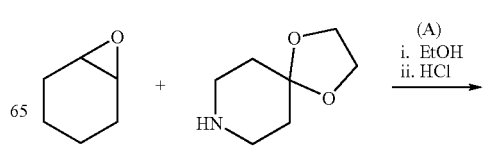

-continued

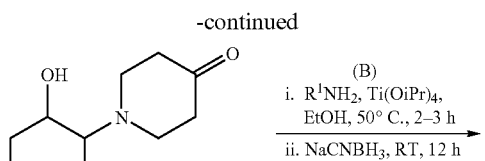

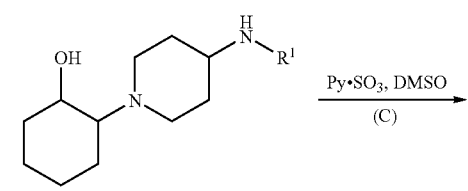

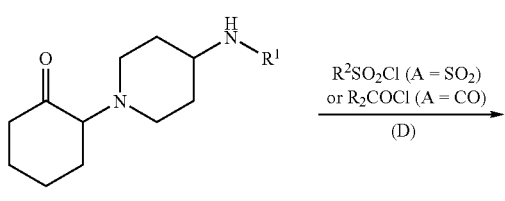

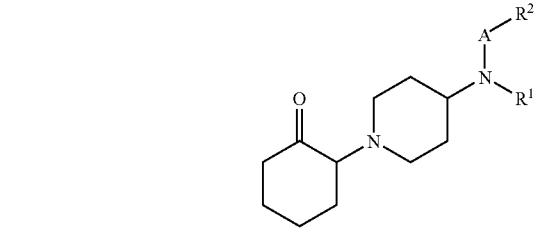

Alternatively, a second synthetic route can be applied to the synthesis of N-[1-(2-oxo-cycloalkyl)-piperidin-4-yl]-N-aryl-arylsulfonamides or N-[1-(2-oxo-cycloalkyl)-piperidin-4-yl]-N-aryl-arylamides, as illustrated in scheme 4. 1-(2-Hydroxy-cyclohexyl)-piperidin-4-one is treated with an amine R¹NH₂ in the presence of titanium tetraisopropoxide and sodium cyanoborohydride (scheme 4, step B). The resulting 2-(4-arylamino-piperidin-1-yl)-cyclohexanol is oxidized with pyridine-sulfur trioxide complex to the corresponding 2-(4-arylamino-piperidin-1-yl)-cyclohexanone (scheme 4, step C). This is either sulfonylated or acylated at the secondary amine as described above, yielding N-[1-(2-oxo-cycloalkyl)-piperidin-4-yl]-N-aryl-arylsulfonamides or N-[1-(2-oxo-cycloalkyl)-piperidin-4-yl]-N-aryl-arylamides (scheme 4, step D).

1-(2-Hydroxy-cyclohexyl)-piperidin-4-one is prepared by reaction of 1,4-dioxa-8-azaspiro[4.5]decane with cyclohexene oxide, followed by hydrolysis of the acetal in acidic conditions as shown in scheme 4, step A.

Scheme 5

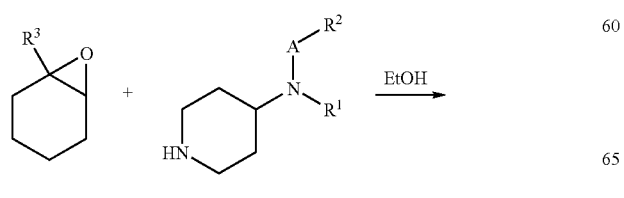

-continued

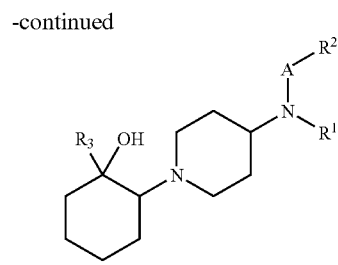

Suitably functionalized piperidines, such as those shown in scheme 3, can also be reacted with 1-aryl-cyclohexene oxide, as shown in scheme 5, to provide compounds of the invention in which the arrangement of substituents of the cylcloalkane ring is trans.

Scheme 6

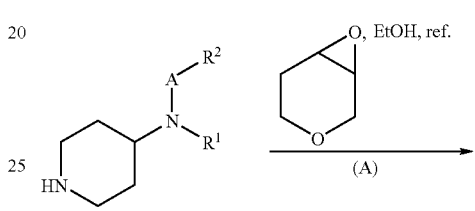

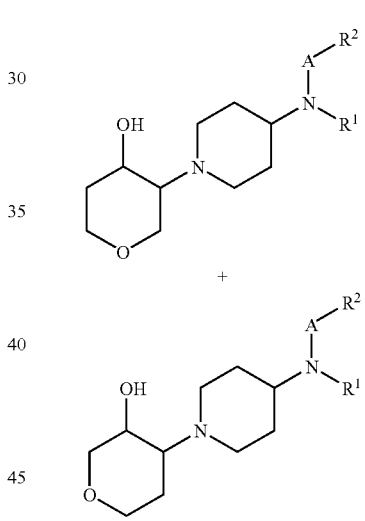

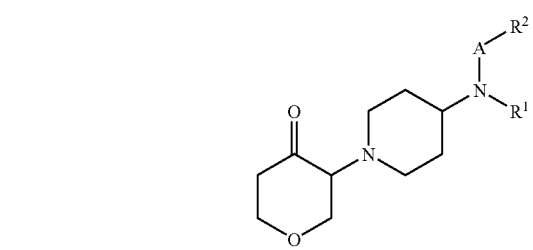

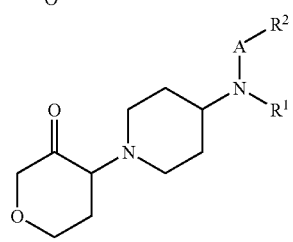

Moreover, suitably functionalized piperidines such as those shown in scheme 3, can also be reacted with (+/−)-3,7-dioxa-bicyclo[4.1.0]heptane (prepared as described in: Tchelitcheff P.; C.R. Hebd. Seances Acad. Sci.; 224; 1947; 1722) (scheme 6, step A), and the resulting alcohols oxidized to the corresponding ketones as described above (scheme 6, step B). Reaction of such ketones with aryl lithium reagents (in analogy to scheme 2, step F), provides compounds of the invention where X or Y is —O—.

3. Preparation of Compounds, wherein $R^2$–$R^4$, X and Y Have the Meaning as Described Above and $R^1$ is Heteroaryl Compounds of formula I where $R^1$ is an heteroaromatic ring and A=CO are also prepared by acylation of the corresponding heteroaromatic amine with a suitable acyl chloride in the presence of a strong non-protic base, as for example 2-tert-butylimino-2-diethylamino-1,3-dimethyl-perhydro-1,3,2-diazaphosphorine (BEMP). For purposes of facilitating purification of the reaction mixtures, also solid phase bound non-protic bases can be used, for example polystyrene-bound BEMP. Secondary heteroaromatic amines of the invention in which $R^1$ is an heteroaromatic ring, in particular an azine ring, are prepared by reacting the corresponding primary amine with a heteroaryl halide, preferably a heteroaryl iodide or bromide in the presence of a base and a catalytic quantity of a suitable palladium complex. The precursor primary amine can be prepared by reductive amination of the corresponding 4-piperidone with a $NH_3$ source, for example by reaction with ammonium formate in the presence of Pd(0), or by other methods known in the art (Scheme 7).

Scheme 7

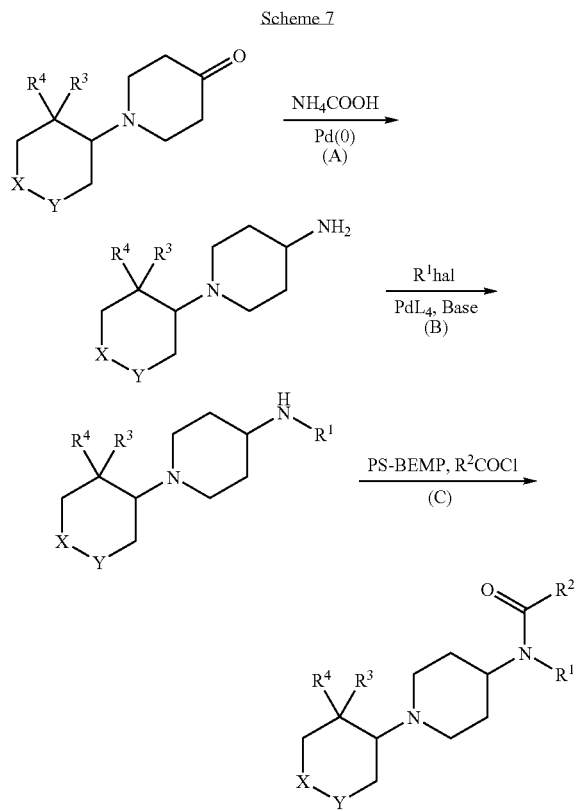

The conversion to a salt of compounds of formula I is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are good inhibitors of the glycine transporter I (GlyT-1).

The compounds were investigated in accordance with the test given hereinafter.

Solutions and Materials

DMEM complete medium: DMEM (Gibco Life-technologies), high glucose, Fetal bovine serum (FBS) 5%, (Gibco life technologies), Penicillin/Streptomycin 1% (Gibco life technologies), Geneticin 1 mg/ml (Gibco life technologies), Proline 19.8 mg/0.5 L of medium (Sigma).

Uptake buffer (UB): 150 mM NaCl, 10 mM Hepes-Tris, pH 7.4, 1 mM $CaCl_2$, 2.5 mM KCl, 2.5 mM $MgSO_4$, 10 mM (+) D-glucose. Chinese Hamster Ovary (CHO) cells stably transfected with hglyT1b cDNA, clone A467-47.

Glycine Uptake Inhibition Assay (hGlyT-1b)

On day 1 mammalian cells, (CHO), transfected with hGlyT-1b cDNA (clone A467-47), were plated at the density of 50,000 cells/well in complete DMEM medium in 96-well culture plates. On day 2, the medium was aspirated and the cells were washed twice with uptake buffer (UB). The cells were then incubated for 30 min at 22° C. with either (i) no potential competitor, (ii) 10 mM non-radioactive glycine, (iii) a concentration of a potential inhibitor. A range of concentrations of the potential inhibitor was used to generate data for calculating the concentration of inhibitor resulting in 50% of the effect (e.g. $IC_{50}$, the concentration of the competitor inhibiting glycine uptake of 50%). A solution was then immediately added containing [$^3$H]-glycine 60 nM (11–16 Ci/mmol) and 25 μM non-radioactive glycine. The cells were then incubated with gentle shaking for 30 min at 22–24° C., after which the reaction was stopped by aspiration of the mixture and washing (three times) with ice-cold UB. The cells were lysed with scintillation liquid, shaken 3 hours and the radioactivity in the cells was counted using a scintillation counter.

The preferred compounds show an $IC_{50}$ (μM) at GlyT-1 in the range of 0.015–0.100, as seen in the table below:

| Example | $IC_{50}$ (μM) |
| --- | --- |
| 1 | 0.048 |
| 3 | 0.094 |
| 11 | 0.056 |
| 17 | 0.049 |
| 22 | 0.083 |

-continued

| Example | IC$_{50}$ (μM) |
|---|---|
| 34 | 0.098 |
| 35 | 0.066 |
| 67 | 0.099 |
| 69 | 0.029 |
| 75 | 0.068 |
| 96 | 0.049 |
| 98 | 0.033 |
| 99 | 0.028 |
| 100 | 0.015 |
| 102 | 0.092 |
| 105 | 0.084 |
| 107 | 0.083 |
| 108 | 0.04 |
| 109 | 0.073 |
| 110 | 0.076 |
| 111 | 0.068 |
| 112 | 0.061 |
| 114 | 0.066 |
| 115 | 0.071 |
| 120 | 0.091 |
| 121 | 0.071 |
| 123 | 0.095 |
| 125 | 0.096 |
| 139 | 0.044 |
| 141 | 0.1 |
| 142 | 0.063 |
| 144 | 0.082 |
| 159 | 0.068 |
| 163 | 0.085 |

The present invention also provides pharmaceutical compositions containing compounds of the invention or pharmaceutically acceptable acid addition salts thereof and a pharmaceutically acceptable carrier. The invention further provides a process for the preparation of such compositions, which comprises bringing one or more compounds of formula I and/or a pharmaceutically acceptable acid addition salt thereof and, if desired, one or more other therapeutically valuable substances into a galenical administration form together with one or more therapeutically inert, pharmaceutically acceptable carriers.

The pharmaceutical compositions can be in the form of tablets, coated tablets, dragées, hard and soft gelatine capsules, solutions emulsions or suspensions. The pharmaceutical compositions also can be in the form of suppositories or injectable solutions.

The compositions of the invention, in addition to one or more compounds of the invention, contain a pharmaceutically acceptable carrier. Suitable pharmaceutically acceptable carriers include pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Compounds of the present invention inhibit glycine transporter 1 (GlyT-1) and have good selectivity to glycine trasporter 2 (GlyT-2) inhibitors. Therefore, the present invention also provides methods for treating disorders related to activation of NMDA receptors via GlyT-1 inhibition. In particular, the present invention provides methods for treating psychoses, schizophrenia, acute mania, depression, bipolar disorders, autistic disorders, cognitive disorders such as dementias, including age related dementia and senile dementia, Alzheimer's disease, memory disorders, attention deficit disorders, and pain. The most preferred indications in accordance with the present invention are those, which include disorders of the central nervous system, for example the treatment or prevention of schizophrenia, cognitive impairment and Alzheimer's disease.

In particular, the present invention provides a method for treating schizophrenia which comprises administering to an individual a therapeutically effective amount of a compound of the invention, for example, a compound of formula I. The present invention also provides a method for treating Alzheimer's disease which comprises administering to an individual a therapeutically effective amount of a compound of the invention, for example, a compound of formula I.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions or suspensions. The pharmaceutical compositions also can be administered rectally, for example, in the form of suppositories or parenterally, for example, in the form of injection solutions.

The dosage at which a compound of the invention is administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

EXAMPLE 1

(+/−)-3,4-Dichloro-N-phenyl-N-[cis-1-(2-phenyl-cyclohexyl)-piperidin-4-yl]-benzenesulfonamide The title compound was prepared as illustrated in scheme 1.

(A) Preparation of (+/−)-cis-1-(2-Phenyl-cyclohexyl)-piperidin-4-one. To a solution of 2-phenyl-cyclohexanone (46.0 g, 264 mmol) and 1,4-dioxa-8-aza-spiro[4,5]decane (31.5 g, 220 mmol) in toluene (380 ml), p-toluenesulphonic acid monohydrate (4.18 g, 22.0 mmol) was added and the mixture was heated to reflux in an apparatus equipped with a Dean-Stark trap for 24 h. The reaction mixture was then evaporated and the resulting crude enamine dissolved in 1,2-dichloroethane (900 ml) and acetic acid (8.00 ml). To this solution, sodium triacetoxyborohydride (69.0 g, 308 mmol) was added in portion. After a total reaction time of 2.5 h, the reaction mixture was treated with 2N NaOH (250 ml) and extracted with dichloromethane. The pooled organic extracts were washed with brine, dried over magnesium sulphate, filtered and evaporated. Purification of the crude product over a silica gel plug (10:1) with n-heptane/ethyl acetate 10:1 then n-heptane/ethyl acetate 9:1 and finally ethyl acetate as eluent provided (+/−)-8-(cis-2-phenyl-cyclohexyl)-1,4-dioxa-8-aza-spiro[4,5]decane (44.8 g, 68%) as a yellow oil, MS (ISP): m/e=302.4 (M+H$^+$).

A solution of (+/−)-8-(cis 2-phenyl-cyclohexyl)-1,4-dioxa-8-aza-spiro[4,5]decane (44.8 g) in MeOH (100 ml) and 6N HCl (445 ml) was heated to reflux for 16 h. The reaction mixture was then made basic with solid sodium carbonate, extracted with dichloromethane, dried over sodium sulphate, filtered and evaporated. The crude product was purified by flash chromatography over silica gel with n-heptane as eluent. (+/−)-1-(cis-2-phenyl-cyclohexyl)-piperidin-4-one (28.8 g, 75%) was obtained as a sticky yellow oil, MS (ISP): m/e=258.3 (M+H$^+$).

(B) Reductive amination to (+/−)-phenyl-[cis-1-(2-phenyl-cyclohexyl)-piperidin-4-yl]-amine. A solution of (+/−)-cis-1-(2-phenyl-cyclohexyl)-piperidin-4-one (0.500 g, 1.94 mmol) and aniline (0.360 g, 3.88 mmol) in technical ethanol (3 ml) was treated with Ti(OiPr)$_4$ (1.10 g, 1.15 ml, 3.88 mmol). The resulting solution was warmed to 60° C. and stirred for 2.5 hours. After cooling to room temperature, sodium cyanoborohydride (0.244 g, 3.88 mmol) was added, and the mixture was stirred at room temperature for 3 hours. The reaction mixture was diluted with dichloromethane (40 ml) and treated under vigorous stirring with NaOH 5N (2 ml) and sodium sulphate (3.0 g). After 15 minutes, white solids separated from a clear solution, which was filtered and evaporated to a crude oil. Purification was achieved by flash chromatography (20–70% ether in dichloromethane). The title amine (0.460 g, 70%) was obtained as a deliquescent white solid, MS (ISP): m/e=335.2 (M+H$^+$).

(C) Sulfonylation to (+/−)-3,4-dichloro-N-phenyl-N-[cis-1-(2-phenyl-cyclohexyl)-piperidin-4-yl]-benzenesulfonamide. A solution of (+/−)-phenyl-[cis-1-(2-phenyl-cyclohexyl)-piperidin-4-yl]-amine (0.105 mg, 0.310 mmol) in dry pyridine (1.5 ml) and dichloromethane (1.0 ml) was treated with a solution of 3,4-dichloro-benzenesulfonyl chloride (0.131 mg, 0.530 mmol) in dichloromethane (1.0 ml), and stirred at room temperature for 24 h. The mixture was then diluted with dichloromethane and quenched with water and sodium hydroxyde 1N (1.0 ml). The phases were separated and the aqueous phase extracted twice with dichloromethane. The combined organic phases were dried with anhydrous sodium sulphate, then concentrated to a crude residue. This was purified by flash chromatography on silica gel, eluting with ethyl acetate 10–30% in heptane. The title compound of the example (0.158 g, 92%) was obtained as an off-white solid, MS (ISP): m/e=543.3 and 545.3 (M+H$^+$).

EXAMPLE 2

(+/−)-3,4-Dichloro-N-phenyl-N-[cis-1-(2-phenyl-cyclohexyl)-piperidin-4-yl]-benzamide The compound of the example was prepared as for example 1 for steps (A) to (B). Step (C) was substituted by the following procedure:

(C) Acylation to (+/−)-3,4-dichloro-N-phenyl-N-[cis-1-(2-phenyl-cyclohexyl)-piperidin-4-yl]-benzamide. A solution of (+/−)-phenyl-[cis-1-(2-phenyl-cyclohexyl)-piperidin-4-yl]-amine (0.017 g, 0.050 mmol), dimethylaminopyridine (0.012 g, 0.010 mmol) and 1-methoxy-2-methyl-1-trimethylsiloxypropene (0.020 ml, 0.10 mmol) in dry tetrahydrofuran (0.5 ml) was treated with a solution of 3,4-dichlorobenzoyl chloride (16 mg, 0.075 mmol) in dry tetrahydrofuran (0.37 ml). The mixture was shaked on a Büchi Syncore Shaker for 20 h, then quenched with water (0.15 ml). The reaction mixture was then injected directly into a preparative HPLC column (YMC ODS-AQ; 50×20 mm; 5 µm; flow: 30 ml/min; run time: 5 min; gradient: 20–80% acetonitrile in water; detection: light scattering). The title compound (7.0 mg, 28%) was obtained as a white solid, MS (ISP): m/e=507.30 (M+H$^+$).

EXAMPLE 3

(+/−)-4-Methoxy-N-(3-methoxy-phenyl)-N-[cis-1-(2-phenyl-cyclohexyl)-piperidin-4-yl]-benzenesulfonamide The title compound, MS (ISP): m/e=535.5 (M+H$^+$), was prepared as for example 1, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 4-methoxy-benzensulfonyl chloride in step (C).

EXAMPLE 4

(+/−)-N-Phenyl-N-[cis-1-(2-phenyl-cyclohexyl)-piperidin-4-yl]-isobutyramide

The title compound, MS (ISP): m/e=405.6 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with 2-methyl-propanoyl chloride in step (C).

EXAMPLE 5

(+/−)-3-Methoxy-N-(3-methoxy-phenyl)-N-[cis-1-(2-phenyl-cyclohexyl)-piperidin-4-yl]-benzamide The title compound, MS (ISP): m/e=499.3 (M+H$^+$), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 3-methoxybenzoyl chloride in step (C).

EXAMPLE 6

(+/−)-N-(3-Methoxy-phenyl)-2-phenyl-N-[cis-1-(2-phenyl-cyclohexyl)-piperidin-4-yl]-acetamide The title compound, MS (ISP): m/e=483.5 (M+H$^+$), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 2-phenyl-acetyl chloride in step (C).

EXAMPLE 7

(+/−)-N-Phenyl-N-[cis-1-(2-phenyl-cyclohexyl)-piperidin-4-yl]-benzamide

The title compound, MS (ISP): m/e=439.5 (M+H$^+$), was prepared as for example 2, steps (A) to (C). Step (B) was performed using aniline, and yielded (+/−)-phenyl-[cis-1-(2- phenyl-cyclohexyl)-piperidin-4-yl]-amine, which was reacted with benzoyl chloride in step (C).

EXAMPLE 8

(+/−)-N-(3-Methoxy-phenyl)-N-[cis-1-(2-phenyl-cyclohexyl)-piperidin-4-yl]-benzamide The title compound, MS (ISP): m/e=469.4 (M+H$^+$), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was then reacted with benzoyl chloride in step (C).

EXAMPLE 9

(+/−)-N-Benzyl-N-[cis-1-(2-phenyl-cyclohexyl)-piperidin-4-yl]-benzamide

The title compound, MS (ISP): m/e=453.6 (M+H$^+$), was prepared as for example 2, steps (A) to (C). Step (B) was performed using benzyl amine, and yielded (+/−)-benzyl-[cis-1-(2-phenyl-cyclohexyl)-piperidin-4-yl]-amine, which was then reacted with benzoyl chloride in step (C).

EXAMPLE 10

(+/−)-N-Phenyl-N-[cis-1-(2-phenyl-cyclohexyl)-piperidin-4-yl]-benzenesulfonamide The title compound, MS (ISP): m/e=475.3 (M+H$^+$), was prepared as for example 1, steps (A) to (C). Step (B) was performed using aniline, and yielded (+/−)-phenyl-[cis-1-(2-phenyl-cyclohexyl)-piperidin-4-yl]-amine, which was reacted with benzensulfonyl chloride in step (C).

EXAMPLE 11

(+/−)-4-Methoxy-N-phenyl-N-[cis-1-(2-phenyl-cyclohexyl)-piperidin-4-yl]-benzenesulfonamide The title compound, MS (ISP): m/e=505.3 (M+H$^+$), was prepared as for example 1, steps (A) to (C). Step (B) was performed using aniline, and yielded (+/−)-phenyl-[cis-1-(2-phenyl-cyclohexyl)-piperidin-4-yl]-amine, which was reacted with 4-methoxy-benzensulfonyl chloride in step (C).

EXAMPLE 12

(+/−)-N-(3-Methoxy-phenyl)-N-[cis-1-(2-phenyl-cyclohexyl)-piperidin-4-yl]-benzenesulfonamide The title compound, MS (ISP): m/e=505.4 (M+H$^+$), was prepared as for example 1, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with benzensulfonyl chloride in step (C).

EXAMPLE 13

(+/−)-N-Benzyl-4-methoxy-N-[cis-1-(2-phenyl-cyclohexyl)-piperidin-4-yl]-benzenesulfonamide The title compound, MS (ISP): m/e=519.3 (M+H$^+$), was prepared as for example 1, steps (A) to (C). Step (B) was performed using benzylamine, and yielded (+/−)-benzyl-[cis-1-(2-phenyl-cyclohexyl)-piperidin-4-yl]-amine, which was reacted with 4-methoxy-benzensulfonyl chloride in step (C).

EXAMPLE 14

(+/−)-N-[cis-1-(2-Phenyl-cyclohexyl)-piperidin-4-yl]-N-p-tolyl-benzamide

The title compound, MS (ISP): m/e=453.6 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with benzoyl chloride in step (C).

EXAMPLE 15

(+/−)-2-Methyl-N-[cis-1-(2-phenyl-cyclohexyl)-piperidin-4-yl]-N-p-tolyl-benzamide The title compound, MS (ISP): m/e=467.4 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 2-methyl-benzoyl chloride in step (C).

EXAMPLE 16

(+/−)-N-[cis-1-(2-Phenyl-cyclohexyl)-piperidin-4-yl]-N-p-tolyl-3-trifluoromethyl-benzamide The title compound, MS (ISP): m/e=521.4 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 3-trifluoromethyl-benzoyl chloride in step (C).

EXAMPLE 17

(+/−)-3-Methoxy-N-[cis-1-(2-phenyl-cyclohexyl)-piperidin-4-yl]-N-p-tolyl-benzamide The title compound, MS (ISP): m/e=483.5 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 3-methoxy-benzoyl chloride in step (C).

EXAMPLE 18

(+/−)-4-Methyl-N-[cis-1-(2-phenyl-cyclohexyl)-piperidin-4-yl]-N-p-tolyl-benzamide The title compound, MS (ISP): m/e=467.4 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 4-methyl-benzoyl chloride in step (C).

EXAMPLE 19

(+/−)-4-Chloro-N-[cis-1-(2-phenyl-cyclohexyl)-piperidin-4-yl]-N-p-tolyl-benzamide The title compound, MS (ISP): m/e=487.4 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 4-chloro-benzoyl chloride in step (C).

EXAMPLE 20

(+/−)-4-Methoxy-N-[cis-1-(2-phenyl-cyclohexyl)-piperidin-4-yl]-N-p-tolyl-benzamide The title compound, MS (ISP): m/e=483.6 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 4-methoxy-benzoyl chloride in step (C).

EXAMPLE 21

(+/−)-3,4-Dichloro-N-[cis-1-(2-phenyl-cyclohexyl)-piperidin-4-yl]-N-p-tolyl-benzamide The title compound, MS (ISP): m/e=521.4, 523.4 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 3,4-dichloro-benzoyl chloride in step (C).

EXAMPLE 22

(+/−)-4-Fluoro-N-[cis-1-(2-phenyl-cyclohexyl)-piperidin-4-yl]-N-p-tolyl-benzamide The title compound, MS (ISP): m/e=471.3 (M+H$^+$), was prepared as for example 2, steps (A) to (C). Step (B) was performed using p-tolyl-amine, and yielded [cis-1-(2-phenyl-cyclohexyl)-piperidin-4-yl]-p-tolyl-amine, which was then reacted with 4-fluoro-benzoyl chloride in step (C).

EXAMPLE 23

(+/−)-N-(4-Methoxy-phenyl)-N-[cis-1-(2-phenyl-cyclohexyl)-piperidin-4-yl]-benzamide The title compound, MS (ISP): m/e=469.4 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with benzoyl chloride in step (C).

EXAMPLE 24

(+/−)-N-(4-Methoxy-phenyl)-2-methyl-N-[cis-1-(2-phenyl-cyclohexyl)-piperidin-4-yl]-benzamide The title compound, MS (ISP): m/e=483.5 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 2-methyl-benzoyl chloride in step (C).

EXAMPLE 25

(+/−)-N-(4-Methoxy-phenyl)-N-[cis-1-(2-phenyl-cyclohexyl)-piperidin-4-yl]-3-trifluoromethyl-benzamide The title compound, MS (ISP): m/e=537.5 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 3-trifluoromethyl-benzoyl chloride in step (C).

EXAMPLE 26

(+/−)-3-Methoxy-N-(4-methoxy-phenyl)-N-[cis-1-(2-phenyl-cyclohexyl)-piperidin-4-yl]-benzamide The title compound, MS (ISP): m/e=499.4 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 3-methoxy-benzoyl chloride in step (C).

EXAMPLE 27

(+/−)-N-(4-Methoxy-phenyl)-4-methyl-N-[cis-1-(2-phenyl-cyclohexyl)-piperidin-4-yl]-benzamide The title compound, MS (ISP): m/e=483.60 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 4-methyl-benzoyl chloride in step (C).

EXAMPLE 28

(+/−)-4-Chloro-N-(4-methoxy-phenyl)-N-[cis-1-(2-phenyl-cyclohexyl)-piperidin-4-yl]-benzamide The title compound, MS (ISP): m/e=503.4 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 4-chloro-benzoyl chloride in step (C).

EXAMPLE 29

(+/−)-3,4-Dichloro-N-(4-methoxy-phenyl)-N-[cis-1-(2-phenyl-cyclohexyl)-piperidin-4-yl]-benzamide The title compound, MS (ISP): m/e=537.4, 539.4 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 3,4-dichloro-benzoyl chloride in step (C).

EXAMPLE 30

(+/−)-4-Fluoro-N-(4-methoxy-phenyl)-N-[cis-1-(2-phenyl-cyclohexyl)-piperidin-4-yl]-benzamide The title compound, MS (ISP): m/e=487.40 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 4-fluoro-benzoyl chloride in step (C).

EXAMPLE 31

(+/−)-Thiophene-2-carboxylic acid (4-methoxy-phenyl)-[cis-1-(2-phenyl-cyclohexyl)-piperidin-4-yl]-amide The title compound, MS (ISP): m/e=475.40 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was then reacted with 2-thiophenecarbonyl chloride in step (C).

EXAMPLE 32

(+/−)-N-(4-Chloro-phenyl)-N-[cis-1-(2-phenyl-cyclohexyl)-piperidin-4-yl]-benzamide The title compound, MS (ISP): m/e=473.3 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with benzoyl chloride in step (C).

EXAMPLE 33

(+/−)-N-(4-Chloro-phenyl)-2-methyl-N-[cis-1-(2-phenyl-cyclohexyl)-piperidin-4-yl]-benzamide The title compound, MS (ISP): m/e=487.4 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 2-methyl-benzoyl chloride in step (C).

EXAMPLE 34

(+/−)-N-(4-Chloro-phenyl)-N-[cis-1-(2-phenyl-cyclohexyl)-piperidin-4-yl]-3-trifluoromethyl-benzamide The title compound, MS (ISP): m/e=541.4 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 3-trifluoromethyl-benzoyl chloride in step (C).

EXAMPLE 35

(+/−)-N-(4-Chloro-phenyl)-3-methoxy-N-[cis-1-(2-phenyl-cyclohexyl)-piperidin-4-yl]-benzamide The title compound, MS (ISP): m/e=503.4 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 3-methoxy-benzoyl chloride in step (C).

EXAMPLE 36

(+/−)-4-Chloro-N-(4-chloro-phenyl)-N-[cis-1-(2-phenyl-cyclohexyl)-piperidin-4-yl]-benzamide The title compound, MS (ISP): m/e=507.5, 509.5 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 4-chloro-benzoyl chloride in step (C).

EXAMPLE 37

(+/−)-N-(4-Chloro-phenyl)-4-methoxy-N-[cis-1-(2-phenyl-cyclohexyl)-piperidin-4-yl]-benzamide The title compound, MS (ISP): m/e=503.5 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 4-methoxy-benzoyl chloride in step (C).

EXAMPLE 38

(+/−)-3,4-Dichloro-N-(4-chloro-phenyl)-N-[cis-1-(2-phenyl-cyclohexyl)-piperidin-4-yl]-benzamide The title compound, MS (ISP): m/e=507.5, 509.5 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 3,4-dichloro-benzoyl chloride in step (C).

EXAMPLE 39

(+/−)-N-(4-Chloro-phenyl)-4-fluoro-N-[cis-1-(2-phenyl-cyclohexyl)-piperidin-4-yl]-benzamide The title compound, MS (ISP): m/e=491.30 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 4-fluoro-benzoyl chloride in step (C).

EXAMPLE 40

(+/−)-Thiophene-2-carboxylic acid (4-chloro-phenyl)-[cis-1-(2-phenyl-cyclohexyl)-piperidin-4-yl]-amide The title compound, MS (ISP): m/e=479.4 (M+H$^+$), was prepared as for example 2, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was then reacted with 2-thiophenecarbonyl chloride in step (C).

EXAMPLE 41

(+/−)-3-Methoxy-N-[cis-1-(2-phenyl-cyclohexyl)-piperidin-4-yl]-N-p-tolyl-benzenesulfonamide The title compound, MS (ISP): m/e=519.4 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 3-methoxy-benzensulfonyl chloride in step (C).

EXAMPLE 42

(+/−)-4-Chloro-N-[cis-1-(2-phenyl-cyclohexyl)-piperidin-4-yl]-N-p-tolyl-benzenesulfonamide The title compound, MS (ISP): m/e=523.3 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 4-chloro-benzensulfonyl chloride in step (C).

EXAMPLE 43

(+/−)-3,4-Dichloro-N-[cis-1-(2-phenyl-cyclohexyl)-piperidin-4-yl]-N-p-tolyl-benzenesulfonamide The title compound, MS (ISP): m/e=557.3, 559.3 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 3,4-dichloro-benzensulfonyl chloride in step (C).

EXAMPLE 44

(+/−)-3,4-Dichloro-N-(4-methoxy-phenyl)-N-[cis-1-(2-phenyl-cyclohexyl)-piperidin-4-yl]-benzene-sulfonamide The title compound, MS (ISP): m/e=573.3, 575.3 (M+H$^+$), was prepared as for example 1, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was reacted with 3,4-dichloro-benzensulfonyl chloride in step (C).

EXAMPLE 45

(+/−)-4-Chloro-N-(4-chloro-phenyl)-N-[cis-1-(2-phenyl-cyclohexyl)-piperidin-4-yl]-benzenesulfonamide The title compound, MS (ISP): m/e=543.3, 545.3 (M+H$^+$), was prepared as for example 1, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was reacted with 4-chloro-benzensulfonyl chloride in step (C).

EXAMPLE 46

(+/−)-N-(4-Chloro-phenyl)-4-methoxy-N-[cis-1-(2-phenyl-cyclohexyl)-piperidin-4-yl]-benzenesulfonamide The title compound, MS (ISP): m/e=539.5 (M+H$^+$), was prepared as for example 1, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was reacted with 4-methoxy-benzensulfonyl chloride in step (C).

EXAMPLE 47

(+/−)-Thiophene-2-sulfonic acid[cis-1-(2-phenyl-cyclohexyl)-piperidin-4-yl]-p-tolyl-amide The title compound, MS (ISP): m/e=495.3 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 2-thiophenyl-sulphonyl chloride in step (C).

EXAMPLE 48

(+/−)-N-[cis-1-(2-phenyl-cyclohexyl)-piperidin-4-yl]-N-p-tolyl-benzenesulfonamide The title compound, MS (ISP): m/e=489.4 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with benzensulfonyl chloride in step (C).

EXAMPLE 49

(+/−)-2-Methyl-N-[cis-1-(2-phenyl-cyclohexyl)-piperidin-4-yl]-N-p-tolyl-benzenesulfonamide The title compound, MS (ISP): m/e=503.5 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 2-methyl-benzensulfonyl chloride in step (C).

EXAMPLE 50

(+/−)-4-Methyl-N-[cis-1-(2-phenyl-cyclohexyl)-piperidin-4-yl]-N-p-tolyl-benzenesulfonamide The title compound, MS (ISP): m/e=503.5 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 4-methyl-benzensulfonyl chloride in step (C).

EXAMPLE 51

(+/−)-N-(4-Chloro-phenyl)-2-methyl-N-[cis-1-(2-phenyl-cyclohexyl)-piperidin-4-yl]-benzenesulfonamide The title compound, MS (ISP): m/e=523.3 (M+H$^+$), was prepared as for example 1, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was reacted with 2-methyl-benzensulfonyl chloride in step (C).

EXAMPLE 52

(+/−)-N-(4-Chloro-phenyl)-3-methoxy-N-[cis-1-(2-phenyl-cyclohexyl)-piperidin-4-yl]-benzenesulfonamide The title compound, MS (ISP): m/e=539.5 (M+H$^+$), was prepared as for example 1, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was reacted with 3-methoxy-benzensulfonyl chloride in step (C).

EXAMPLE 53

(+/−)-N-(4-Chloro-phenyl)-4-methyl-N-[cis-1-(2-phenyl-cyclohexyl)-piperidin-4-yl]-benzenesulfonamide The title compound, MS (ISP): m/e=523.3 (M+H$^+$), was prepared as for example 1, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was reacted with 4-methyl-benzensulfonyl chloride in step (C).

EXAMPLE 54

(+/−)-3,4-Dichloro-N-(4-chloro-phenyl)-N-[cis-1-(2-phenyl-cyclohexyl)-piperidin-4-yl]-benzenesulfonamide The title compound, MS (ISP): m/e=577.1, 579.1 (M+H$^+$), was prepared as for example 1, steps (A) to (C). Step (B) was performed using 4-chloro-aniline, and yielded (+/−)-(4-chloro-phenyl)-[cis-1-(2-phenyl-cyclohexyl)-piperidin-4-yl]-amine, which was reacted with 3,4-dichloro-benzensulfonyl chloride in step (C).

EXAMPLE 55

(+/−)-N-[cis-1-(2-phenyl-cyclohexyl)-piperidin-4-yl]-N-p-tolyl-3-trifluoromethyl-benzenesulfonamide The title compound, MS (ISP): m/e=557.5 (M+H$^+$), was prepared as for example 1, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 3-trifluoromethyl-benzensulfonyl chloride in step (C).

EXAMPLE 56

(+/−)-N-(4-Methoxy-phenyl)-N-[cis-1-(2-phenyl-cyclohexyl)-piperidin-4-yl]-benzenesulfonamide The title compound, MS (ISP): m/e=505.4 (M+H$^+$), was prepared as for example 1, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was reacted with benzensulfonyl chloride in step (C).

EXAMPLE 57

(+/−)-N-(4-Methoxy-phenyl)-2-methyl-N-[cis-1-(2-phenyl-cyclohexyl)-piperidin-4-yl]-benzenesulfonamide The title compound, MS (ISP): m/e=519.5 (M+H$^+$), was prepared as for example 1, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was reacted with 2-methyl-benzensulfonyl chloride in step (C).

EXAMPLE 58

(+/−)-N-(4-Methoxy-phenyl)-4-methyl-N-[cis-1-(2-phenyl-cyclohexyl)-piperidin-4-yl]-benzenesulfonamide The title compound, MS (ISP): m/e=519.4 (M+H$^+$), was prepared as for example 1, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was reacted with 4-methyl-benzensulfonyl chloride in step (C).

EXAMPLE 59

(+/−)-4-Chloro-N-(4-methoxy-phenyl)-N-[cis-1-(2-phenyl-cyclohexyl)-piperidin-4-yl]-benzenesulfonamide The title compound, MS (ISP): m/e=539.4 (M+H$^+$), was prepared as for example 1, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was reacted with 4-chloro-benzensulfonyl chloride in step (C).

EXAMPLE 60

(+/−)-N-(3,4-Dichloro-phenyl)-4-methoxy-N-[cis-1-(2-phenyl-cyclohexyl)-piperidin-4-yl]-benzene-sulfonamide The title compound, MS (ISP): m/e=573.3, 575.3 (M+H$^+$), was prepared as for example 1, steps (A) to (C). Step (B) was performed using 3,4-dichloro-aniline, and yielded (+/−)-(3,4-dichloro-phenyl)-[cis-1-(2-phenyl-cyclohexyl)-piperidin-4-yl]-amine, which was reacted with 4-methoxy-benzensulfonyl chloride in step (C).

EXAMPLE 61

(+/−)-4-Chloro-N-(3-methoxy-phenyl)-N-[cis-1-(2-phenyl-cyclohexyl)-piperidin-4-yl]-benzenesulfonamide The title compound, MS (ISP): m/e=539.5 (M+H$^+$), was prepared as for example 1, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 4-chloro-benzensulfonyl chloride in step (C).

EXAMPLE 62

(+/−)-N-(3-Methoxy-phenyl)-4-methyl-N-[cis-1-(2-phenyl-cyclohexyl)-piperidin-4-yl]-benzenesulfonamide The title compound, MS (ISP): m/e=519.5 (M+H$^+$), was prepared as for example 1, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 4-methyl-benzensulfonyl chloride in step (C).

EXAMPLE 63

(+/−)-3,4-Dichloro-N-(3-methoxy-phenyl)-N-[cis-1-(2-phenyl-cyclohexyl)-piperidin-4-yl]-benzene-sulfonamide The title compound, MS (ISP): m/e=573.3, 575.3 (M+H$^+$), was prepared as for example 1, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 3,4-dichloro-benzensulfonyl chloride in step (C).

EXAMPLE 64

(+/−)-4-Fluoro-N-(3-methoxy-phenyl)-N-[cis-1-(2-phenyl-cyclohexyl)-piperidin-4-yl]-benzenesulfonamide The title compound, MS (ISP): m/e=523.3 (M+H$^+$), was prepared as for example 1, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 4-fluoro-benzensulfonyl chloride in step (C).

EXAMPLE 65

(+/−)-N-(3-Methoxy-phenyl)-2-methyl-N-[cis-1-(2-phenyl-cyclohexyl)-piperidin-4-yl]-benzenesulfonamide The title compound, MS (ISP): m/e=519.4 (M+H$^+$), was prepared as for example 1, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 2-methyl-benzensulfonyl chloride in step (C).

EXAMPLE 66

(+/−)-4-Chloro-N-(4-fluoro-phenyl)-N-[cis-1-(2-phenyl-cyclohexyl)-piperidin-4-yl]-benzenesulfonamide The title compound, MS (ISP): m/e=527.3 (M+H$^+$), was prepared as for example 1, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was reacted with 4-chloro-benzensulfonyl chloride in step (C).

EXAMPLE 67

(+/−)-N-(4-Fluoro-phenyl)-4-methyl-N-[cis-1-(2-phenyl-cyclohexyl)-piperidin-4-yl]-benzenesulfonamide The title compound, MS (ISP): m/e=507.5 (M+H$^+$), was prepared as for example 1, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was reacted with 4-methyl-benzensulfonyl chloride in step (C).

EXAMPLE 68

(+/−)-3,4-Dichloro-N-(4-fluoro-phenyl)-N-[cis-1-(2-phenyl-cyclohexyl)-piperidin-4-yl]-benzenesulfonamide The title compound, MS (ISP): m/e=561.4, 563.4 (M+H$^+$), was prepared as for example 1, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was reacted with 3,4-dichloro-benzensulfonyl chloride in step (C).

EXAMPLE 69

(+/−)-N-(4-Fluoro-phenyl)-4-methoxy-N-[cis-1-(2-phenyl-cyclohexyl)-piperidin-4-yl]-benzenesulfonamide The title compound, MS (ISP): m/e=523.3 (M+H$^+$), was prepared as for example 1, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was reacted with 4-methoxy-benzensulfonyl chloride in step (C).

EXAMPLE 70

(+/−)-4-Fluoro-N-(4-fluoro-phenyl)-N-[cis-1-(2-phenyl-cyclohexyl)-piperidin-4-yl]-benzenesulfonamide The title compound, MS (ISP): m/e=511.4 (M+H$^+$), was prepared as for example 1, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was reacted with 4-fluoro-benzensulfonyl chloride in step (C).

EXAMPLE 71

(+/−)-N-(4-Fluoro-phenyl)-N-[cis-1-(2-phenyl-cyclohexyl)-piperidin-4-yl]-benzenesulfonamide The title compound, MS (ISP): m/e=493.3 (M+H$^+$), was prepared as for example 1, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was reacted with benzensulfonyl chloride in step (C).

EXAMPLE 72

(+/−)-N-(4-Fluoro-phenyl)-2-methyl-N-[cis-1-(2-phenyl-cyclohexyl)-piperidin-4-yl]-benzenesulfonamide The title compound, MS (ISP): m/e=507.5 (M+H$^+$), was prepared as for example 1, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was reacted with 2-methyl-benzensulfonyl chloride in step (C).

EXAMPLE 73

(+/−)-4-Chloro-N-[cis-1-(2-phenyl-cyclohexyl)-piperidin-4-yl]-N-(3-trifluoromethyl-phenyl)-benzenesulfonamide The title compound, MS (ISP): m/e=577.3 (M+H$^+$), was prepared as for example 1, steps (A) to (C). Step (B) was performed using 3-trifluoromethyl-aniline, and yielded (+/−)-[cis-1-(2-phenyl-cyclohexyl)-piperidin-4-yl]-(3-trifluoromethyl-phenyl)-amine, which was reacted with 4-chloro-benzensulfonyl chloride in step (C).

EXAMPLE 74

(+/−)-4-Methyl-N-[cis-1-(2-phenyl-cyclohexyl)-piperidin-4-yl]-N-(3-trifluoromethyl-phenyl)-benzenesulfonamide The title compound, MS (ISP): m/e=557.4 (M+H$^+$), was prepared as for example 1, steps (A) to (C). Step (B) was performed using 3-trifluoromethyl-aniline, and yielded (+/−)-[cis-1-(2-phenyl-cyclohexyl)-piperidin-4-yl]-(3-trifluoromethyl-phenyl)-amine, which was reacted with 4-methyl-benzensulfonyl chloride in step (C).

EXAMPLE 75

(+/−)-4-Methoxy-N-[cis-1-(2-phenyl-cyclohexyl)-piperidin-4-yl]-N-(3-trifluoromethyl-phenyl)-benzenesulfonamide The title compound, MS (ISP): m/e=573.4 (M+H$^+$), was prepared as for example 1, steps (A) to (C). Step (B) was performed using 3-trifluoromethyl-aniline, and yielded (+/−)-[cis-1-(2-phenyl-cyclohexyl)-piperidin-4-yl]-(3-trifluoromethyl-phenyl)-amine, which was reacted with 4-methoxy-benzensulfonyl chloride in step (C).

EXAMPLE 76

(+/−)-4-Fluoro-N-[cis-1-(2-phenyl-cyclohexyl)-piperidin-4-yl]-N-(3-trifluoromethyl-phenyl)-benzenesulfonamide The title compound, MS (ISP): m/e=561.5 (M+H$^+$), was prepared as for example 1, steps (A) to (C). Step (B) was performed using 3-trifluoromethyl-aniline, and yielded (+/−)-[cis-1-(2-phenyl-cyclohexyl)-piperidin-4-yl]-(3-trifluoromethyl-phenyl)-amine, which was reacted with 4-fluoro-benzensulfonyl chloride in step (C).

EXAMPLE 77

(+/−)-N-[cis-1-(2-phenyl-cyclohexyl)-piperidin-4-yl]-N-(3-trifluoromethyl-phenyl)-benzenesulfonamide The title compound, MS (ISP): m/e=543.4 (M+H$^+$), was prepared as for example 1, steps (A) to (C). Step (B) was performed using 3-trifluoromethyl-aniline, and yielded (+/−)-[cis-1-(2-phenyl-cyclohexyl)-piperidin-4-yl]-(3-trifluoromethyl-phenyl)-amine, which was reacted with benzensulfonyl chloride in step (C).

EXAMPLE 78

(+/−)-2-Methyl-N-[cis-1-(2-phenyl-cyclohexyl)-piperidin-4-yl]-N-(3-trifluoromethyl-phenyl)-benzenesulfonamide The title compound, MS (ISP): m/e=557.5 (M+H$^+$), was prepared as for example 1, steps (A) to (C). Step (B) was performed using 3-trifluoromethyl-aniline, and yielded (+/−)-[cis-1-(2-phenyl-cyclohexyl)-piperidin-4-yl]-(3-trifluoromethyl-phenyl)-amine, which was reacted with 2-methyl-benzensulfonyl chloride in step (C).

EXAMPLE 79

(+/−)-4-Chloro-N-[cis-1-(2-phenyl-cyclohexyl)-piperidin-4-yl]-N-o-tolyl-benzenesulfonamide The title compound, MS (ISP): m/e=523.3 (M+H$^+$), was prepared as for example 1, steps (A) to (C). Step (B) was performed using o-tolyl-amine, and yielded (+/−)-[cis-1-(2-phenyl-cyclohexyl)-piperidin-4-yl]-o-tolyl-amine, which was reacted with 4-chloro-benzensulfonyl chloride in step (C).

EXAMPLE 80

(+/−)-4-Methyl-N-[cis-1-(2-phenyl-cyclohexyl)-piperidin-4-yl]-N-o-tolyl-benzenesulfonamide The title compound, MS (ISP): m/e=503.5 (M+H$^+$), was prepared as for example 1, steps (A) to (C). Step (B) was performed using o-tolyl-amine, and yielded (+/−)-[cis-1-(2-phenyl-cyclohexyl)-piperidin-4-yl]-o-tolyl-amine, which was reacted with 4-methyl-benzensulfonyl chloride in step (C).

EXAMPLE 81

(+/−)-3,4-Dichloro-N-[cis-1-(2-phenyl-cyclohexyl)-piperidin-4-yl]-N-o-tolyl-benzenesulfonamide The title compound, MS (ISP): m/e=557.4, 559.4 (M+H$^+$), was prepared as for example 1, steps (A) to (C). Step (B) was performed using o-tolyl-amine, and yielded (+/−)-[cis-1-(2-phenyl-cyclohexyl)-piperidin-4-yl]-o-tolyl-amine, which was reacted with 3,4-dichloro-benzensulfonyl chloride in step (C).

EXAMPLE 82

(+/−)-4-Methoxy-N-[cis-1-(2-phenyl-cyclohexyl)-piperidin-4-yl]-N-o-tolyl-benzenesulfonamide The title compound, MS (ISP): m/e=519.5 (M+H$^+$), was prepared as for example 1, steps (A) to (C). Step (B) was performed using o-tolyl-amine, and yielded (+/−)-[cis-1-(2-phenyl-cyclohexyl)-piperidin-4-yl]-o-tolyl-amine, which was reacted with 4-methoxy-benzensulfonyl chloride in step (C).

EXAMPLE 83

(+/−)-4-Fluoro-N-[cis-1-(2-phenyl-cyclohexyl)-piperidin-4-yl]-N-o-tolyl-benzenesulfonamide The title compound, MS (ISP): m/e=507.5 (M+H$^+$), was prepared as for example 1, steps (A) to (C). Step (B) was performed using o-tolyl-amine, and yielded (+/−)-[cis-1-(2-phenyl-cyclohexyl)-piperidin-4-yl]-o-tolyl-amine, which was reacted with 4-fluoro-benzensulfonyl chloride in step (C).

EXAMPLE 84

(+/−)-N-[cis-1-(2-phenyl-cyclohexyl)-piperidin-4-yl]-N-o-tolyl-benzenesulfonamide The title compound, MS (ISP): m/e=489.5 (M+H$^+$), was prepared as for example 1, steps (A) to (C). Step (B) was performed using o-tolyl-amine, and yielded (+/−)-[cis-1-(2-phenyl-cyclohexyl)-piperidin-4-yl]-o-tolyl-amine, which was reacted with benzensulfonyl chloride in step (C).

EXAMPLE 85

(+/−)-2-Methyl-N-[cis-1-(2-phenyl-cyclohexyl)-piperidin-4-yl]-N-o-tolyl-benzenesulfonamide The title compound, MS (ISP): m/e=503.5 (M+H$^+$), was prepared as for example 1, steps (A) to (C). Step (B) was performed using o-tolyl-amine, and yielded (+/−)-[cis-1-(2-phenyl-cyclohexyl)-piperidin-4-yl]-o-tolyl-amine, which was reacted with 2-methyl-benzensulfonyl chloride in step (C).

EXAMPLE 86

(+/−)-4-Chloro-N-phenyl-N-[cis-1-(2-phenyl-cyclohexyl)-piperidin-4-yl]-benzenesulfonamide The title compound, MS (ISP): m/e=509.5 (M+H$^+$), was prepared as for example 1, steps (A) to (C). Step (B) was performed using aniline, and yielded (+/−)-phenyl-[cis-1-(2-phenyl-cyclohexyl)-piperidin-4-yl]-amine, which was reacted with 4-chloro-benzensulfonyl chloride in step (C).

EXAMPLE 87

(+/−)-4-Methyl-N-phenyl-N-[cis-1-(2-phenyl-cyclohexyl)-piperidin-4-yl]-benzenesulfonamide The title compound, MS (ISP): m/e=489.4 (M+H$^+$), was prepared as for example 1, steps (A) to (C). Step (B) was performed using aniline, and yielded (+/−)-phenyl-[cis-1-(2-phenyl-cyclohexyl)-piperidin-4-yl]-amine, which was reacted with 4-methyl-benzensulfonyl chloride in step (C).

EXAMPLE 88

(+/−)-4-Fluoro-N-phenyl-N-[cis-1-(2-phenyl-cyclohexyl)-piperidin-4-yl]-benzenesulfonamide The title compound, MS (ISP): m/e=493.3 (M+H$^+$), was prepared as for example 1, steps (A) to (C). Step (B) was performed using aniline, and yielded (+/−)-phenyl-[cis-1-(2-phenyl-cyclohexyl)-piperidin-4-yl]-amine, which was reacted with 4-fluoro-benzensulfonyl chloride in step (C).

EXAMPLE 89

(+/−)-2-Methyl-N-phenyl-N-[cis-1-(2-phenyl-cyclohexyl)-piperidin-4-yl]-benzenesulfonamide The title compound, MS (ISP): m/e=489.5 (M+H$^+$), was prepared as for example 1, steps (A) to (C). Step (B) was performed using aniline, and yielded (+/−)-phenyl-[cis-1-(2-phenyl-cyclohexyl)-piperidin-4-yl]-amine, which was reacted with 2-methyl-benzensulfonyl chloride in step (C).

EXAMPLE 90

(+/−)-N-Benzyl-4-chloro-N-[cis-1-(2-phenyl-cyclohexyl)-piperidin-4-yl]-benzenesulfonamide The title compound, MS (ISP): m/e=523.3 (M+H$^+$), was prepared as for example 1, steps (A) to (C). Step (B) was performed using benzylamine, and yielded (+/−)-benzyl-[cis-1-(2-phenyl-cyclohexyl)-piperidin-4-yl]-amine, which was reacted with 4-chloro-benzensulfonyl chloride in step (C).

EXAMPLE 91

(+/−)-N-Benzyl-4-methyl-N-[cis-1-(2-phenyl-cyclohexyl)-piperidin-4-yl]-benzenesulfonamide The title compound, MS (ISP): m/e=503.5 (M+H$^+$), was prepared as for example 1, steps (A) to (C). Step (B) was performed using benzylamine, and yielded (+/−)-benzyl-[cis-1-(2-phenyl-cyclohexyl)-piperidin-4-yl]-amine, which was reacted with 4-methyl-benzensulfonyl chloride in step (C).

EXAMPLE 92

(+/−)-N-(3,4-Dichloro-phenyl)-2-methyl-N-[cis-1-(2-phenyl-cyclohexyl)-piperidin-4-yl]-benzene-sulfonamide The title compound, MS (ISP): m/e=557.4, 559.4 (M+H$^+$), was prepared as for example 1, steps (A) to (C). Step (B) was performed using 3,4-dichloro-aniline, and yielded (+/−)-(3,4-dichloro-phenyl)-[cis-1-(2-phenyl-cyclohexyl)-piperidin-4-yl]-amine, which was reacted with 2-methyl-benzensulfonyl chloride in step (C).

EXAMPLE 93

(+/−)-4-Chloro-N-(3,4-dichloro-phenyl)-N-[cis-1-(2-phenyl-cyclohexyl)-piperidin-4-yl]-benzenesulfonamide The title compound, MS (ISP): m/e=577.2, 579.2 (M+H$^+$), was prepared as for example 1, steps (A) to (C). Step (B) was performed using 3,4-dichloro-aniline, and yielded (+/−)-(3,4-dichloro-phenyl)-[cis-1-(2-phenyl-cyclohexyl)-piperidin-4-yl]-amine, which was reacted with 4-chloro-benzenesulfonyl chloride in step (C).

EXAMPLE 94

(+/−)-4-Nitro-N-phenyl-N-[cis-1-(2-phenyl-cyclohexyl)-piperidin-4-yl]-benzenesulfonamide The title compound, MS (ISP): m/e=520.3 (M+H$^+$), was prepared as for example 1, steps (A) to (C). Step (B) was performed using aniline, and yielded (+/−)-Phenyl-[cis-1-(2-phenyl-cyclohexyl)-piperidin-4-yl]-amine, which was reacted with 4-nitro-benzenesulfonyl chloride in step (C).

EXAMPLE 95

(+/−)-4-Amino-N-phenyl-N-[cis-1-(2-phenyl-cyclohexyl)-piperidin-4-yl]-benzenesulfonamide The title compound, MS (ISP): m/e=490.3 (M+H$^+$), was prepared by hydrogenation of (+/−)-4-nitro-N-phenyl-N-[cis-1-(2-phenyl-cyclohexyl)-piperidin-4-yl]-benzenesulfonamide according to the following procedure. (+/−)-4-Nitro-N-phenyl-N-[cis-1-(2-phenyl-cyclohexyl)-piperidin-4-yl]-benzenesulfonamide (0.05 g, 0.096 mmol) was suspended in isopropanol (3 ml) and the mixture was purged with argon. Palladium hydroxide on charcoal was added to the suspension, which was then put under a hydrogen atmosphere and stirred at room temperature for 20 h. The catalyst was then filtered off and the solvent was evaporated, leaving the title compound as a white foamy solid (0.039 g, 82%).

EXAMPLE 96

(+)-4-Methoxy-N-phenyl-N-[cis-1-(2-phenyl-cyclohexyl)-piperidin-4-yl]-benzenesulfonamide The title compound, MS (ISP): m/e=505.5 (M+H$^+$), was obtained by chromatographic separation of (+/−)-4-methoxy-N-phenyl-N-[cis-1-(2-phenyl-cyclohexyl)-piperidin-4-yl]-benzenesulfonamide on a chiral column [Chiralpak AD, solution: ethanol (2 ml)/heptane (3 ml), elution: 5% isopropanol in heptane, flux: 35 ml/min, wavelength: 245 nm, retention time: 26.73 min.]

EXAMPLE 97

(−)-4-Methoxy-N-phenyl-N-[cis-1-(2-phenyl-cyclohexyl)-piperidin-4-yl]-benzenesulfonamide The title compound, MS (ISP): m/e=505.5 (M+H$^+$), was obtained by chromatographic separation of (+/−)-4-methoxy-N-phenyl-N-[cis-1-(2-phenyl-cyclohexyl)-piperidin-4-yl]-benzenesulfonamide on a chiral column [Chiralpak AD, solution: ethanol (2 ml)/heptane (3 ml), elution: 5% isopropanol in heptane, flux: 35 ml/min, wavelength: 245 nm, retention time: 32.5 min.]

EXAMPLE 98

(+/−)-N-(4-Fluoro-phenyl)-N-[cis-1-(2-hydroxy-2-phenyl-cyclohexyl)-piperidin-4-yl]-3-methoxy-benzamide The title compound was prepared as illustrated in schemes 2 and 3.

(A) Reductive amination to 4-(4-fluoro-phenylamino)-piperidine-1-carboxylic acid tert-butyl ester. To a solution of 1-Boc-4-piperidone (10.0 g, 50.0 mmol) in 1,2-dichloroethane (100 ml) was added 4-fluoroaniline (5.60 g, 50.0 mmol), acetic acid (6.20 ml, 103 mmol) and sodium triacetoxyborohydride (16.8 g, 75.3 mmol). After stirring at room temperature for 18 hours, the reaction mixture was quenched with sodium hydroxide 1N (200 ml). The aqueous phase was extracted with dichloromethane, the combined organic layers were dried over anhydrous sodium sulphate, filtered and concentrated in vacuo. The residue was taken up in ether to provide a precipitate. Filtration led to 4-(4-fluoro-phenylamino)-piperidine-1-carboxylic acid tert-butyl ester (11.1 g, 75%) as an off white solid, MS (ISP): m/e=295.3 (M+H$^+$).

(B) Acylation to 4-[(4-fluoro-phenyl)-(3-methoxy-benzoyl)-amino]-piperidine-1-carboxylic acid tert-butyl ester. To a solution of 4-(4-fluoro-phenylamino)-piperidine-1-carboxylic acid tert-butyl ester (5.0 g, 17 mmol) in dichloromethane (60 ml) was added triethylamine (5.9 ml, 42 mmol), 4-dimethylaminopyridine (0.21 g, 1.7 mmol) and 3-methoxybenzoyl chloride (3.5 g, 20 mmol). After stirring at room temperature for 20 hours, the reaction mixture was quenched with saturated sodium hydrogencarbonate (50 ml). The aqueous phase was extracted with dichloromethane, the combined organic layers were dried over anhydrous sodium sulphate, filtered and concentrated in vacuo. The residue was taken in ether to provide a precipitate. Filtration led to 4-[(4-fluoro-phenyl)-(3-methoxy-benzoyl)-amino]-piperidine-1-carboxylic acid tert-butyl ester (6.2 g, 84%) as a white solid, MS (ISP): m/e=429.3 (M+H$^+$).

(C) Deprotection to N-(4-fluoro-phenyl)-3-methoxy-N-piperidin-4-yl-benzamide. To a 0° C. solution of 4-[(4-fluoro-phenyl)-(3-methoxy-benzoyl)-amino]-piperidine-1- carboxylic acid tert-butyl ester (6.0 g, 14 mmol) in dichloromethane (60 ml) was added trifluoroacetic acid (11 ml, 141 mmol). After 1.5 hours stirring at room temperature, the reaction mixture was concentrated in vacuo. The residue was taken in dichloromethane and sodium hydroxide (1N). The aqueous phase was extracted with dichloromethane, the combined organic layers were dried over anhydrous sodium sulphate, filtered and concentrated in vacuo. The residue was taken in ether to provide a precipitate. Filtration led to N-(4-fluoro-phenyl)-3-methoxy-N-piperidin-4-yl-benzamide (4.2 g, 90%) as a light yellow solid, MS (ISP): m/e=329.3 (M+H+).

(D) Preparation of (+/−)-N-(4-fluoro-phenyl)-N-[trans-1-(2-hydroxy-cyclohexyl)-piperidin-4-yl]-3-methoxy-benzamide. To a solution of N-(4-fluoro-phenyl)-3-methoxy-N-piperidin-4-yl-benzamide (3.0 g, 9.1 mmol) in ethanol (30 ml) was added cyclohexene oxide (0.90 ml, 9.1 mmol). The reaction mixture was refluxed for 44 hours then cooled to room temperature and concentrated. The residue was boiled in ether for 1 hour then cooled to room temperature to provide a precipitate. Filtration led to (+/−)-N-(4-fluoro-phenyl)-N-[trans-1-(2-hydroxy-cyclohexyl)-piperidin-4-yl]-3-methoxy-benzamide (3.5 g, 90%) as a light yellow solid, MS (ISP): m/e=427.3 (M+H+).

(E) Oxidation to (+/−)-N-(4-fluoro-phenyl)-3-methoxy-N-[1-(2-oxo-cyclohexyl)-piperidin-4-yl]-benzamide. To a solution of (+/−)-N-(4-fluoro-phenyl)-N-[trans-1-(2-hydroxy-cyclohexyl)-piperidin-4-yl]-3-methoxy-benzamide (1.0 g, 2.3 mmol) in dichloromethane (6.0 ml) and dimethylsulfoxide (6.0 ml) was added triethylamine (1.6 ml, 12 mmol). The reaction mixture was cooled to 0° C. and a solution of sulfur trioxide-pyridine complex (1.1 g, 7.0 mmol) in dimethylsulfoxide was added dropwise. After 2 hours stirring at RT, the reaction mixture was poured into water and dichloromethane. The aqueous phase was extracted with dichloromethane, the combined organic layers were dried over anhydrous sodium sulphate, filtered and concentrated in vacuo. The residue was chromatographed over silica gel ($CH_2Cl_2$—MeOH 97:3) to provide (+/−)-N-(4-fluoro-phenyl)-3-methoxy-N-[1-(2-oxo-cyclohexyl)-piperidin-4-yl]-benzamide (0.82 g, 83%) as a white solid, MS (ISP): m/e=425.3 (M+H+).

(F) Preparation of (+/−)-N-(4-fluoro-phenyl)-N-[cis-1-(2-hydroxy-2-phenyl-cyclohexyl)-piperidin-4-yl]-3-methoxy-benzamide. To a −78° C. solution of (+/−)-N-(4-fluorophenyl)-3-methoxy-N-[1-(2-oxo-cyclohexyl)-piperidin-4-yl]-benzamide (0.13 g, 0.30 mmol) in tetrahydrofuran (2.5 ml) was added phenyl lithium (1.7 M solution in cyclohexane/ether, 0.18 ml, 0.30 mmol,). After 40 min. stirring at −78° C., the reaction mixture was quenched with saturated ammonium chloride (5 ml) and the aqueous phase was extracted with ethyl acetate. The combined organic layers were dried over anhydrous sodium sulphate, filtered and concentrated in vacuo. The residue was chromatographed over silica gel ($CH_2Cl_2$/MeOH 99:1) to provide (+/−)-N-(4-fluoro-phenyl)-N-[cis-1-(2-hydroxy-2-phenyl-cyclohexyl)-piperidin-4-yl]-3-methoxy-benzamide (0.050 g, 34%) as a white foam, MS (ISP): m/e=503.4 (M+H+).

EXAMPLE 99

(+/−)-N-[cis-1-(2-Hydroxy-2-phenyl-cyclohexyl)-piperidin-4-yl]-4-methoxy-N-phenyl-benzenesulfonamide The title compound was prepared according to the procedure illustrated in schemes 2 and 4.

(A) Preparation of (+/−)-trans-1-(2-hydroxy-cyclohexyl)-piperidin-4-one. To a solution of 1,4-dioxa-8-azaspiro[4,5]decane (14.7 g, 100 mmol) in ethanol (75 ml) was added cyclohexene oxide (10.0 g, 100 mmol). The reaction mixture was refluxed for 40 hours then cooled to room temperature and concentrated. The residue was chromatographed over silica gel (hexane/ethylacetate 4:1) to provide (+/−)-trans-2-(1,4-dioxa-8-aza-spiro[4.5]dec-8-yl)-cyclohexanol (22.1 g, 91%) as a white solid, MS (ISP): m/e=241.2 (M+).

A solution of (+/−)-trans-2-(1,4-dioxa-8-aza-spiro[4.5]dec-8-yl)-cyclohexanol (1.50 g, 6.25 mmol) in dioxane (45 ml) was treated with 5N hydrogen chloride (10 ml). The mixture was warmed to 105° C. and stirred for 4 h. After cooling to room temperature, water (9 ml) was added to the mixture, which was then basified to pH 14 by slow addition of 5N sodium hydroxide. The mixture was then extracted three times with ethyl acetate and the combined organic extracts were dried with anhydrous sodium sulphate and concentrated. The residual oil was purified by flash chromatography on silica gel, eluting with methanol 0–5% in dichloromethane. (+/−)-trans-1-(2-Hydroxy-cyclohexyl)-piperidin-4-one (0.830 g, 68%) was obtained as a white solid, MS (ISP): m/e=198.3 (M+H+).

(B) Reductive amination to (+/−)-trans-2-(4-phenylamino-piperidin-1-yl)-cyclohexanol. A solution of (+/−)-trans-1-(2-hydroxy-cyclohexyl)-piperidin-4-one (0.68, 3.4 mmol) in ethanol (4 ml) was treated with aniline (0.32 g, 3.4 mmol) and titanium tetraisopropoxide (1.2 g, 4.1 mmol). The mixture was warmed to 38° C. and stirred for 15 h. After cooling to 0° C. by means of an ice/water bath, sodium borohydride (0.19 g, 5.1 mmol) was added in portions, whereupon vigorous hydrogen evolution took place. The resulting slurry was diluted with ethanol (4 ml) and stirred at room temperature for 3 h. The reaction was further diluted with ethanol and quenched with 1N sodium hydroxide. The two phases were separated and the aqueous phase was extracted with dichloromethane. The combined organic extracts were dried with anhydrous sodium sulphate and concentrated. The residue was purified by flash chromatography on a silica gel column and eluted with methanol 0–10% in dichloromethane. (+/−)-trans-2-(4-Phenylamino-piperidin-1-yl)-cyclohexanol (0.50 g, 53%) was obtained as a white solid, MS (ISP): m/e=275.4 (M+H+)

(C) Oxidation to (+/−)-2-(4-phenylamino-piperidin-1-yl)-cyclohexanone. A solution of (+/−)-trans-2-(4-phenylamino-piperidin-1-yl)-cyclohexanol (0.22 g, 0.81 mmol) in dry dimethylsulfoxide (4.8 ml) was treated with triethylamine (0.41 g, 4.1 mmol). A solution of pyridine-sulfur trioxide complex (0.39 g, 2.4 mmol), which had been dried for one night in a vacuum pump, in dry dimethylsulfoxide (1.9 ml) was added dropwise to the mixture over 3 min. The solution was stirred at room temperature for 1 h, then quenched with water (50 ml). The mixture was extracted four times with ethyl acetate (4×20 ml). The combined organic phases were washed twice with water (2×20 ml), then dried with anhydrous sodium sulphate and concentrated to a colorless oil. Purification was achieved by chromatography on silica gel, eluting with methanol 0–10% in dichloromethane. (+/−)-2-(4-Phenylamino-piperidin-1-yl)-cyclohexanone (0.12 g, 53%) was obtained as an off-white solid, MS (ISP): m/e=273.4 (M+H+).

(D) Sulphonylation to (+/−)-4-methoxy-N-[1-(2-oxo-cyclohexyl)-piperidin-4-yl]-N-phenyl-benzenesulfonamide. (+/−)-2-(4-Phenylamino-piperidin-1-yl)-cyclohexanone was sulphonylated with 4-methoxy-benzensulphonyl chloride, as in example 1, step (C). (+/−)-4-Methoxy-N-[1-(2-oxo-cyclohexyl)-piperidin-4-yl]-N-phenyl-benzenesulfonamide, MS(ISP): m/e 443.5 (M+H⁺), was obtained as a white foamy solid.

(F) Preparation of (+/−)-N-[cis-1-(2-hydroxy-2-phenyl-cyclohexyl)-piperidin-4-yl]-4-methoxy-N-phenyl-benzenesulfonamide. A solution of bromobenzene (0.16 g, 1.0 mmol) in dry tetrahydrofuran (2.1 ml) was cooled to −70° C. and a solution of butyl lithium 1.6 M in hexanes (0.65 ml, 1.0 mmol) was added dropwise. The resulting solution was stirred at −70° C. for 1 h, then treated with a solution of (+/−)-4-methoxy-N-[1-(2-oxo-cyclohexyl)-piperidin-4-yl]-N-phenyl-benzenesulfonamide (0.12 mg, 0.26 mmol) in dry tetrahydrofuran (2.1 ml). The reaction mixture was stirred at −70° C. for 1 h, then warmed slowly to room temperature and stirred for 10 min. After cooling to −78° C., the reaction was quenched with 20% ammonium chloride (3.4 ml). The two phases were separated, and the aqueous phase extracted twice with ethyl acetate. The combined organic extracts were dried with anhydrous sodium sulphate and concentrated. The residue was purified by flash chromatography on silica gel, eluting with methanol 0–5% in dichloromethane. (+/−)-N-[cis-1-(2-hydroxy-2-phenyl-cyclohexyl)-piperidin-4-yl]-4-methoxy-N-phenyl-benzenesulfonamide, MS(ISP): m/e 521.5 (M+H⁺), was obtained as a white foamy solid (0.093 g, 69%).

EXAMPLE 100

(+)-N-[cis-1-(2-Hydroxy-2-phenyl-cyclohexyl)-piperidin-4-yl]-4-methoxy-N-phenyl-benzenesulfonamide The title compound, MS (ISP): m/e=521.5 (M+H⁺), was obtained by chromatographic separation of (+/−)-N-[cis-1-(2-hydroxy-2-phenyl-cyclohexyl)-piperidin-4-yl]-4-methoxy-N-phenyl-benzenesulfonamide on a chiral column [Chiralpak AD, solution: ethanol (2 ml)/heptane (3 ml), elution: 10% ethanol in heptane, flux: 35 ml/min, wavelength: 245 nm, retention time: 29.64 min.].

EXAMPLE 101

(−)-N-[cis-1-(2-Hydroxy-2-phenyl-cyclohexyl)-piperidin-4-yl]-4-methoxy-N-phenyl-benzenesulfonamide The title compound, MS (ISP): m/e=521.5 (M+H⁺), was obtained by chromatographic separation of (+/−)-N-[cis-1-(2-hydroxy-2-phenyl-cyclohexyl)-piperidin-4-yl]-4-methoxy-N-phenyl-benzenesulfonamide on a chiral column [Chiralpak AD, solution: ethanol (2 ml)/heptane (3 ml), elution: 10% ethanol in heptane, flux: 35 ml/min, wavelength: 245 nm, retention time: 39.56 min.].

EXAMPLE 102

(+/−)-N-(4-Chloro-phenyl)-N-[cis-1-(2-Hydroxy-2-phenyl-cyclohexyl)-piperidin-4-yl]-4-methoxy-benzenesulfonamide The title compound, MS (ISP): m/e=555.3 (M+H⁺), was prepared as for example 99, steps (A) to (F). Step (B) was performed using 4-chloro-aniline, and yielded (+/−)-trans-2-[4-(4-chloro-phenylamino)-piperidin-1-yl]-cyclohexanol, which was oxidized to (+/−)-2-[4-(4-chloro-phenylamino)-piperidin-1-yl]-cyclohexanone in step (C). This was then reacted with 4-methoxy-benzensulfonyl chloride in step (D), yielding (+/−)-N-(4-chloro-phenyl)-4-methoxy-N-[1-(2-oxo-cyclohexyl)-piperidin-4-yl]-benzenesulfonamide. The final step (F) was performed with bromobenzene.

EXAMPLE 103

(+/−)-N-(4-Chloro-phenyl)-N-{cis-1-[2-(4-chloro-phenyl)-2-hydroxy-cyclohexyl]-piperidin-4-yl}-4-methoxy-benzenesulfonamide The title compound, MS (ISP): m/e=589.3 (M+H⁺), was prepared as for example 102, steps (A) to (F). The final step (F) was performed with 4-bromo-chlorobenzene.

EXAMPLE 104

(+/−)-N-(4-Chloro-phenyl)-N-{cis-1-[2-(4-fluoro-phenyl)-2-hydroxy-cyclohexyl]-piperidin-4-yl}-4-methoxy-benzenesulfonamide The title compound, MS (ISP): m/e=573.3 (M+H⁺), was prepared as for example 102, steps (A) to (F). The final step (F) was performed with 4-bromo-fluorobenzene.

EXAMPLE 105

(+/−)-N-(4-Chloro-phenyl)-N-[cis-1-(2-hydroxy-2-pyridin-3-yl-cyclohexyl)-piperidin-4-yl]-4-methoxy-benzenesulfonamide The title compound, MS (ISP): m/e=556.3 (M+H⁺), was prepared as for example 102, steps (A) to (F). The final step (F) was performed with 3-bromo-pyridine.

EXAMPLE 106

(+/−)-N-(4-Chloro-phenyl)-N-[cis-1-(2-Hydroxy-2-o-tolyl-cyclohexyl)-piperidin-4-yl]-4-methoxy-benzenesulfonamide The title compound, MS (ISP): m/e=569.4 (M+H⁺), was prepared as for example 102, steps (A) to (F). The final step (F) was performed with 2-bromo-toluene.

EXAMPLE 107

(+/−)-N-{cis-1-[2-(4-Chloro-phenyl)-2-hydroxy-cyclohexyl]-piperidin-4-yl}-4-methoxy-N-phenyl-benzenesulfonamide The title compound, MS (ISP): m/e=555.3 (M+H⁺), was prepared as for example 99, steps (A) to (F). The final step (F) was performed with 4-bromo-chlorobenzene.

EXAMPLE 108

(+/−)-N-{cis-1-[2-(4-Fluoro-phenyl)-2-hydroxy-cyclohexyl]-piperidin-4-yl}-4-methoxy-N-phenyl-benzenesulfonamide The title compound, MS (ISP): m/e=539.4 (M+H⁺), was prepared as for example 99, steps (A) to (F). The final step (F) was performed with 4-bromo-fluorobenzene.

EXAMPLE 109

(+/−)-N-[cis-1-(2-Hydroxy-2-pyridin-4-yl-cyclo-hexyl)-piperidin-4-yl]-4-methoxy-N-phenyl-benze-nesulfonamide The title compound, MS (ISP): m/e=522.4 (M+H$^+$), was prepared as for example 99, steps (A) to (F). The final step (F) was performed with 4-bromo-pyridine.

EXAMPLE 110

(+/−)-N-[cis-1-(2-Hydroxy-2-pyridin-3-yl-cyclo-hexyl)-piperidin-4-yl]-4-methoxy-N-phenyl-benze-nesulfonamide The title compound, MS (ISP): m/e=522.4 (M+H$^+$), was prepared as for example 99, steps (A) to (F). The final step (F) was performed with 3-bromo-pyridine.

EXAMPLE 111

(+/−)-N-[cis-1-(2-Hydroxy-2-o-tolyl-cyclohexyl)-piperidin-4-yl]-4-methoxy-N-phenyl-benzene-sulfonamide The title compound, MS (ISP): m/e=535.4 (M+H$^+$), was prepared as for example 99, steps (A) to (F). The final step (F) was performed with 2-bromo-toluene.

EXAMPLE 112

(+/−)-N-(4-Fluoro-phenyl)-N-[cis-1-(2-Hydroxy-2-phenyl-cyclohexyl)-piperidin-4-yl]-4-methoxy-ben-zenesulfonamide The title compound, MS (ISP): m/e=539.4 (M+H$^+$), was prepared as for example 99, steps (A) to (F). Step (B) was performed using 4-fluoro-aniline, and yielded (+/−)-trans-2-[4-(4-fluoro-phenylamino)-piperidin-1-yl]-cyclohexanol, which was oxidized to (+/−)-2-[4-(4-fluoro-phenylamino)-piperidin-1-yl]-cyclohexanone in step (C). This was then reacted with 4-methoxy-benzensulfonyl chloride in step (D), yielding (+/−)-N-(4-fluoro-phenyl)-4-methoxy-N-[1-(2-oxo-cyclohexyl)-piperidin-4-yl]-benzenesulfonamide. The final step (F) was performed with bromobenzene.

EXAMPLE 113

(+/−)-N-{cis-1-[2-(4-Chloro-phenyl)-2-hydroxy-cyclohexyl]-piperidin-4-yl}-N-(4-fluoro-phenyl)-4-methoxy-benzenesulfonamide The title compound, MS (ISP): m/e=573.3 (M+H$^+$), was prepared as for example 112, steps (A) to (F). The final step (F) was performed with 4-bromo-chlorobenzene.

EXAMPLE 114

(+/−)-N-(4-Fluoro-phenyl)-N-{cis-1-[2-(4-fluoro-phenyl)-2-hydroxy-cyclohexyl]-piperidin-4-yl}-4-methoxy-benzenesulfonamide The title compound, MS (ISP): m/e=557.3 (M+H$^+$), was prepared as for example 112, steps (A) to (F). The final step (F) was performed with 4-bromo-fluorobenzene.

EXAMPLE 115

(+/−)-N-(4-Fluoro-phenyl)-N-[cis-1-(2-hydroxy-2-pyridin-4-yl-cyclohexyl)-piperidin-4-yl]-4-methoxy-benzenesulfonamide The title compound, MS (ISP): m/e=540.4 (M+H$^+$), was prepared as for example 112, steps (A) to (F). The final step (F) was performed with 4-bromo-pyridine.

EXAMPLE 116

(+/−)-N-(4-Fluoro-phenyl)-N-[cis-1-(2-hydroxy-2-pyridin-3-yl-cyclohexyl)-piperidin-4-yl]-4-methoxy-benzenesulfonamide The title compound, MS (ISP): m/e=540.4 (M+H$^+$), was prepared as for example 112, steps (A) to (F). The final step (F) was performed with 3-bromo-pyridine.

EXAMPLE 117

(+/−)-N-[cis-1-(2-Hydroxy-2-phenyl-cyclohexyl)-piperidin-4-yl]-4-methoxy-N-(3-trifluoromethyl-phenyl)-benzenesulfonamide The title compound, MS (ISP): m/e=589.4 (M+H$^+$), was prepared as for example 99, steps (A) to (F). Step (B) was performed using 4-trifluoromethyl-aniline, and yielded (+/−)-trans-2-[4-(4-trifluoromethyl-phenylamino)-piperidin-1-yl]-cyclohexanol, which was oxidized to (+/−)-2-[4-(4-trifluoromethyl-phenylamino)-piperidin-1-yl]-cyclohexanone in step (C). This was then reacted with 4-methoxy-benzensulfonyl chloride in step (D), yielding (+/−)-N-(4-trifluoromethyl-phenyl)-4-methoxy-N-[1-(2-oxo-cyclohexyl)-piperidin-4-yl]-benzenesulfonamide. The final step (F) was performed with bromobenzene.

EXAMPLE 118

(+/−)-N-{cis-1-[2-(4-Chloro-phenyl)-2-hydroxy-cyclohexyl]-piperidin-4-yl}-4-methoxy-N-(3-trifluoromethyl-phenyl)-benzenesulfonamide The title compound, MS (ISP): m/e=623.4 (M+H$^+$), was prepared as for example 117, steps (A) to (F). The final step (F) was performed with 4-bromo-chlorobenzene.

EXAMPLE 119

(+/−)-N-{cis-1-[2-(4-Fluoro-phenyl)-2-hydroxy-cyclohexyl]-piperidin-4-yl}-4-methoxy-N-(3-trifluoromethyl-phenyl)-benzenesulfonamide The title compound, MS (ISP): m/e=607.3 (M+H$^+$), was prepared as for example 117, steps (A) to (F). The final step (F) was performed with 4-bromo-fluorobenzene.

EXAMPLE 120

(+/−)-N-[cis-1-(2-Hydroxy-2-pyridin-4-yl-cyclo-hexyl)-piperidin-4-yl]-4-methoxy-N-(3-trifluorom-ethyl-phenyl)-benzenesulfonamide The title compound, MS (ISP): m/e=590.40 (M+H$^+$), was prepared as for example 117, steps (A) to (F). The final step (F) was performed with 4-bromo-pyridine.

EXAMPLE 121

(+/−)-N-[cis-1-(2-Hydroxy-2-pyridin-3-yl-cyclohexyl)-piperidin-4-yl]-4-methoxy-N-(3-trifluoromethyl-phenyl)-benzenesulfonamide The title compound, MS (ISP): m/e=590.40 (M+H$^+$), was prepared as for example 117, steps (A) to (F). The final step (F) was performed with 3-bromo-pyridine.

EXAMPLE 122

(+/−)-N-[cis-1-(2-Hydroxy-2-o-tolyl-cyclohexyl)-piperidin-4-yl]-4-methoxy-N-(3-trifluoromethyl-phenyl)-benzenesulfonamide The title compound, MS (ISP): m/e=603.4 (M+H$^+$), was prepared as for example 117, steps (A) to (F). The final step (F) was performed with 2-bromo-toluene.

EXAMPLE 123

(+/−)-N-[cis-1-(2-Hydroxy-2-phenyl-cyclohexyl)-piperidin-4-yl]-4-methoxy-N-(3-methoxy-phenyl)-benzenesulfonamide The title compound, MS (ISP): m/e=551.4 (M+H$^+$), was prepared as for example 99, steps (A) to (F). Step (B) was performed using 3-methoxy-aniline, and yielded (+/−)-trans-2-[4-(3-methoxy-phenylamino)-piperidin-1-yl]-cyclohexanol, which was oxidized to (+/−)-2-[4-(3-methoxy-phenylamino)-piperidin-1-yl]-cyclohexanone in step (C). This was then reacted with 4-methoxy-benzensulfonyl chloride in step (D), yielding (+/−)-N-(3-methoxy-phenyl)-4-methoxy-N-[1-(2-oxo-cyclohexyl)-piperidin-4-yl]-benzenesulfonamide. The final step (F) was performed with bromobenzene.

EXAMPLE 124

(+/−)-N-{cis-1-[2-(4-Chloro-phenyl)-2-hydroxy-cyclohexyl]-piperidin-4-yl}-4-methoxy-N-(3-methoxy-phenyl)-benzenesulfonamide The title compound, MS (ISP): m/e=585.3 (M+H$^+$), was prepared as for example 123, steps (A) to (F). The final step (F) was performed using 4-chloro-bromobenzene.

EXAMPLE 125

(+/−)-N-{cis-1-[2-(4-Fluoro-phenyl)-2-hydroxy-cyclohexyl]-piperidin-4-yl}-4-methoxy-N-(3-methoxy-phenyl)-benzenesulfonamide The title compound, MS (ISP): m/e=569.4 (M+H$^+$), was prepared as for example 123, steps (A) to (F). The final step (F) was performed using 4-fluoro-bromobenzene.

EXAMPLE 126

(+/−)-N-[cis-1-(2-Hydroxy-2-pyridin-4-yl-cyclohexyl)-piperidin-4-yl]-4-methoxy-N-(3-methoxy-phenyl)-benzenesulfonamide The title compound, MS (ISP): m/e=552.4 (M+H$^+$), was prepared as for example 123, steps (A) to (F). The final step (F) was performed using 4-bromopyridine.

EXAMPLE 127

(+/−)-N-[cis-1-(2-Hydroxy-2-pyridin-3-yl-cyclohexyl)-piperidin-4-yl]-4-methoxy-N-(3-methoxy-phenyl)-benzenesulfonamide The title compound, MS (ISP): m/e=552.4 (M+H$^+$), was prepared as for example 124, steps (A) to (F). The final step (F) was performed using 3-bromopyridine.

EXAMPLE 128

(+/−)-4-Chloro-N-[cis-1-(2-Hydroxy-2-phenyl-cyclohexyl)-piperidin-4-yl]-N-phenyl-benzenesulfonamide The title compound, MS (ISP): m/e=525.3 (M+H$^+$), was prepared as for example 99, steps (A) to (F). Step (D) was performed using 4-chloro-benzenesulphonyl chloride, and yielded (+/−)-4-chloro-N-[1-(2-oxo-cyclohexyl)-piperidin-4-yl]-N-phenyl-benzensulfonamide. The final step (F) was performed with bromobenzene.

EXAMPLE 129

(+/−)-4-Chloro-N-{cis-1-[2-(4-chloro-phenyl)-2-hydroxy-cyclohexyl]-piperidin-4-yl}-N-phenyl-benzenesulfonamide The title compound, MS (ISP): m/e=559.30 (M+H$^+$), was prepared as for example 128, steps (A) to (F). The final step (F) was performed using 4-chloro-bromobenzene.

EXAMPLE 130

(+/−)-4-Chloro-N-{cis-1-[2-(4-fluoro-phenyl)-2-hydroxy-cyclohexyl]-piperidin-4-yl}-N-phenyl-benzenesulfonamide The title compound, MS (ISP): m/e=543.4 (M+H$^+$), was prepared as for example 128, steps (A) to (F). The final step (F) was performed using 4-fluoro-bromobenzene.

EXAMPLE 131

(+/−)-4-Chloro-N-[cis-1-(2-hydroxy-2-pyridin-4-yl-cyclohexyl)-piperidin-4-yl]-N-phenyl-benzenesulfonamide The title compound, MS (ISP): m/e=526.3 (M+H$^+$), was prepared as for example 128, steps (A) to (F). The final step (F) was performed using 4-bromopyridine.

EXAMPLE 132

(+/−)-4-Chloro-N-[cis-1-(2-hydroxy-2-pyridin-3-yl-cyclohexyl)-piperidin-4-yl]-N-phenyl-benzenesulfonamide The title compound, MS (ISP): m/e=526.3 (M+H$^+$), was prepared as for example 128, steps (A) to (F). The final step (F) was performed using 3-bromopyridine.

EXAMPLE 133

(+/−)-4-Chloro-N-[cis-1-(2-Hydroxy-2-α-tolyl-cyclohexyl)-piperidin-4-yl]-N-phenyl-benzenesulfonamide The title compound, MS (ISP): m/e=539.4 (M+H$^+$), was prepared as for example 128, steps (A) to (F). The final step (F) was performed using 2-bromotoluene.

EXAMPLE 134

(+/−)-3,4-Dichloro-N-[cis-1-(2-hydroxy-2-phenyl-cyclohexyl)-piperidin-4-yl]-N-phenyl-benzene-sulfonamide The title compound, MS (ISP): m/e=559.3 (M+H$^+$), was prepared as for example 99, steps (A) to (F). Step (D) was performed using 3,4-dichloro-benzenesulphonyl chloride, and yielded (+/−)-3,4-dichloro-N-[1-(2-oxo-cyclohexyl)-piperidin-4-yl]-N-phenyl-benzensulfonamide. The final step (F) was performed with bromobenzene.

EXAMPLE 135

(+/−)-3,4-Dichloro-N-{cis 1-[2-(4-chloro-phenyl)-2-hydroxy-cyclohexyl]-piperidin-4-yl}-N-phenyl-benzenesulfonamide The title compound, MS (ISP): m/e=593.3 (M+H$^+$), was prepared as for example 134, steps (A) to (F). The final step (F) was performed using 4-chloro-bromobenzene.

EXAMPLE 136

(+/−)-3,4-Dichloro-N-{cis-1-[2-(4-fluoro-phenyl)-2-hydroxy-cyclohexyl]-piperidin-4-yl}-N-phenyl-benzenesulfonamide The title compound, MS (ISP): m/e=577.3 (M+H$^+$), was prepared as for example 134, steps (A) to (F). The final step (F) was performed using 4-fluoro-bromobenzene.

EXAMPLE 137

(+/−)-3,4-Dichloro-N-[cis-1-(2-hydroxy-2-pyridin-3-yl-cyclohexyl)-piperidin-4-yl]-N-phenyl-benzenesulfonamide The title compound, MS (ISP): m/e=560.2 (M+H$^+$), was prepared as for example 135, steps (A) to (F). The final step (F) was performed using 3-bromopyridine.

EXAMPLE 138

(+/−)-3,4-Dichloro-N-[cis-1-(2-Hydroxy-2-o-tolyl-cyclohexyl)-piperidin-4-yl]-N-phenyl-benzenesulfonamide The title compound, MS (ISP): m/e=573.2 (M+H$^+$), was prepared as for example 134, steps (A) to (F). The final step (F) was performed using 2-bromotoluene.

EXAMPLE 139

(+/−)-N-(4-Chloro-phenyl)-N-[cis-1-(2-Hydroxy-2-phenyl-cyclohexyl)-piperidin-4-yl]-3-methoxy-benzamide The title compound, MS (ISP): m/e=519.4 (M+H$^+$), white foam, was prepared as for example 98, steps (A) to (F). Step (A) was performed using 4-chloro-aniline, and yielded 4-(4-chloro-phenylamino)-piperidine-1-carboxylic acid tert-butyl ester which was acylated to 4-[(4-chloro-phenyl)-(3-methoxy-benzoyl)-amino]-piperidine-1-carboxylic acid tert-butyl ester in step (B). This was then deprotected to N-(4-chloro-phenyl)-3-methoxy-N-piperidin-4-yl-benzamide (C), and reacted with cyclohexene oxide to give (+/−)—N-(4-chloro-phenyl)-N-[trans-1-(2-hydroxy-cyclohexyl)-piperidin-4-yl]-3-methoxy-benzamide [step (D)]. Oxidation to (+/−)-N-(4-chloro-phenyl)-3-methoxy-N-[1-(2-oxo-cyclohexyl)-piperidin-4-yl]-benzamide in step (E) and reaction with phenyl lithium [step (F)] led to the title compound of the example.

EXAMPLE 140

(+/−)-N-[cis-1-(2-Hydroxy-2-o-tolyl-cyclohexyl)-piperidin-4-yl]-4-methoxy-N-(3-methoxy-phenyl)-benzenesulfonamide The title compound, MS (ISP): m/e=565.4 (M+H$^+$), was prepared as for example 123, steps (A) to (F). The final step (F) was performed using 2-bromotoluene.

EXAMPLE 141

(+/−)-4-Fluoro-N-[cis-1-(2-Hydroxy-2-phenyl-cyclohexyl)-piperidin-4-yl]-N-p-tolyl-benzamide The title compound, MS (ISP): m/e=487.4 (M+H$^+$), was prepared as for example 98, steps (A) to (F). Step (A) was performed using 4-tolylamine, and yielded 4-p-Tolylamino-piperidine-1-carboxylic acid tert-butyl ester which was acylated with 4-fluorobenzoyl chloride to 4-[(4-fluoro-benzoyl)-p-tolyl-amino]-piperidine-1-carboxylic acid tert-butyl ester in step (B). This was then deprotected to 4-fluoro-N-piperidin-4-yl-N-p-tolyl-benzamide (C), and reacted with cyclohexene oxide to give (+/−)-4-fluoro-N-[trans-1-(2-hydroxy-cyclohexyl)-piperidin-4-yl]-N-p-tolyl-benzamide [step (D)]. Oxidation to (+/−)-4-fluoro-N-[1-(2-oxo-cyclohexyl)-piperidin-4-yl]-N-p-tolyl-benzamide in step (E) and reaction with phenyl lithium [step (F)] led to the title compound of the example.

EXAMPLE 142

(+/−)-N-[cis-1-(2-Hydroxy-2-phenyl-cyclohexyl)-piperidin-4-yl]-N-(3-methoxy-phenyl)-benzamide The title compound, MS (ISP): m/e=485.4 (M+H$^+$), was prepared as for example 98, steps (A) to (F). Step (A) was performed using 3-methoxy-aniline, and yielded 4-(3-methoxy-phenylamino)-piperidine-1-carboxylic acid tert-butyl ester which was acylated with benzoyl chloride to 4-[benzoyl-(3-methoxy-phenyl)-amino]-piperidine-1-carboxylic acid tert-butyl ester (B). This was then deprotected to N-(3-methoxy-phenyl)-N-piperidin-4-yl-benzamide (C), and reacted with cyclohexene oxide to gave (+/−)-N-[trans-1-(2-hydroxy-cyclohexyl)-piperidin-4-yl]-N-(3-methoxyphenyl)-benzamide [step (D)]. Oxidation to (+/−)-N-(3-methoxy-phenyl)-N-[1-(2-oxo-cyclohexyl)-piperidin-4-yl]-benzamide in step (E) and reaction with phenyl lithium [step (F)] led to the title compound of the example.

EXAMPLE 143

(+/−)-3-Methoxy-N-phenyl-N-[cis-1-(2-phenyl-cyclohexyl)-piperidin-4-yl]-benzamide The title compound, MS (ISP): m/e=469.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was then reacted with 3-methoxy-benzoyl chloride in step (C).

EXAMPLE 144

(+/−)-N-[cis-1-(2-Hydroxy-2-phenyl-cyclohexyl)-piperidin-4-yl]-3-methoxy-N-p-tolyl-benzamide The title compound, MS (ISP): m/e=499.0 (M+H$^+$), was prepared as for example 141, steps (A) to (F). Step (B) was performed using 3-methoxybenzoyl chloride, and yielded 4-[(3-methoxy-benzoyl)-p-tolyl-amino]-piperidine-1-carboxylic acid tert-butyl ester. This was then deprotected to 3-methoxy-N-piperidin-4-yl-N-p-tolyl-benzamide (step C), and reacted with cyclohexene oxide to give (+/−)-N-[trans-1-(2-hydroxy-cyclohexyl)-piperidin-4-yl]-3-methoxy-N-p-tolyl-benzamide [step (D)]. Oxidation to (+/−)-3-methoxy-N-[1-(2-oxo-cyclohexyl)-piperidin-4-yl]-N-p-tolyl-benzamidein step (E) and reaction with phenyl lithium [step (F)] led to the title compound of the example.

EXAMPLE 145

(+/−)-4-Fluoro-N-phenyl-N-[cis-1-(2-phenyl-cyclohexyl)-piperidin-4-yl]-benzamide The title compound, MS (ISP): m/e=457.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was then reacted with 4-fluoro-benzoyl chloride in step (C).

EXAMPLE 146

(+/−)-N-Phenyl-N-[cis-1-(2-phenyl-cyclohexyl)-piperidin-4-yl]-3-trifluoromethyl-benzamide The title compound, MS (ISP): m/e=507.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was then reacted with 3-trifluoro-benzoyl chloride in step (C).

EXAMPLE 147

(+/−)-3-Methoxy-N-(3-methoxy-phenyl)-N-[cis-1-(2-phenyl-cyclohexyl)-piperidin-4-yl]-benzamide The title compound, MS (ISP): m/e=499.4 (M+H$^+$), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was then reacted with 3-methoxy-benzoyl chloride in step (C).

EXAMPLE 148

(+/−)-4-Fluoro-N-(3-methoxy-phenyl)-N-[cis-1-(2-phenyl-cyclohexyl)-piperidin-4-yl]-benzamide The title compound, MS (ISP): m/e=487.4 (M+H$^+$), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was then reacted with 4-fluoro-benzoyl chloride in step (C).

EXAMPLE 149

(+/−)-N-(3-Methoxy-phenyl)-N-[cis-1-(2-phenyl-cyclohexyl)-piperidin-4-yl]-3-trifluoromethyl-benzamide The title compound, MS (ISP): m/e=537.4 (M+H$^+$), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was then reacted with 3-trifluoro-benzoyl chloride in step (C).

EXAMPLE 150

(+/−)-3,4-Dichloro-N-(3-methoxy-phenyl)-N-[cis-1-(2-phenyl-cyclohexyl)-piperidin-4-yl]-benzamide The title compound, MS (ISP): m/e=537.4 (M+H$^+$), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was then reacted with 3,4-dichloro-benzoyl chloride in step (C).

EXAMPLE 151

(+/−)-N-(4-Fluoro-phenyl)-3-methoxy-N-[cis-1-(2-phenyl-cyclohexyl)-piperidin-4-yl]-benzamide The title compound, MS (ISP): m/e=487.5 (M+H$^+$), was prepared as for example 2, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was then reacted with 3-methoxy-benzoyl chloride in step (C).

EXAMPLE 152

(+/−)-4-Fluoro-N-(4-fluoro-phenyl)-N-[cis-1-(2-phenyl-cyclohexyl)-piperidin-4-yl]-benzamide The title compound, MS (ISP): m/e=475.3 (M+H$^+$), was prepared as for example 2, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was then reacted with 4-fluoro-benzoyl chloride in step (C).

EXAMPLE 153

(+/−)-N-(4-Fluoro-phenyl)-N-[cis-1-(2-phenyl-cyclohexyl)-piperidin-4-yl]-3-trifluoromethyl-benzamide The title compound, MS (ISP): m/e=525.4 (M+H$^+$), was prepared as for example 2, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was then reacted with 3-trifluoro-benzoyl chloride in step (C).

EXAMPLE 154

(+/−)-3,4-Dichloro-N-(4-fluoro-phenyl)-N-[cis-1-(2-phenyl-cyclohexyl)-piperidin-4-yl]-benzamide The title compound, MS (ISP): m/e=525.3 (M+H$^+$), was prepared as for example 2, steps (A) to (C). Step (B) was performed using 4-fluoro-aniline, and yielded (+/−)-(4-fluoro-phenyl)-[cis-1-(2-phenyl-cyclohexyl)-piperidin-4-yl]-amine, which was then reacted with 3,4-dichloro-benzoyl chloride in step (C).

EXAMPLE 155

(+/−)-4-Fluoro-N-[cis-1-(2-phenyl-cyclohexyl)-piperidin-4-yl]-N-(3-trifluoromethyl-phenyl)-benzamide The title compound, MS (ISP): m/e=525.4 (M+H$^+$), was prepared as for example 2, steps (A) to (C). Step (B) was performed using 3-trifluoro-aniline, and yielded (+/−)-[cis-1-(2-phenyl-cyclohexyl)-piperidin-4-yl]-(3-trifluoromethyl-phenyl)-amine, which was then reacted with 4-fluoro-benzoyl chloride in step (C).

EXAMPLE 156

(+/−)-N-[cis-1-(2-Phenyl-cyclohexyl)-piperidin-4-yl]-3-trifluoromethyl-N-(3-trifluoromethyl-phenyl)-benzamide The title compound, MS (ISP): m/e=575.3 (M+H$^+$), was prepared as for example 2, steps (A) to (C). Step (B) was performed using 3-trifluoro-aniline, and yielded (+/−)-[cis-1-(2-phenyl-cyclohexyl)-piperidin-4-yl]-(3-trifluoromethyl-phenyl)-amine, which was then reacted with 3-trifluoro-benzoyl chloride in step (C).

EXAMPLE 157

(+/−)-4-Hydroxy-N-phenyl-N-[cis-1-(2-phenyl-cyclohexyl)-piperidin-4-yl]-benzenesulfonamide A solution of (+/−)-4-methoxy-N-phenyl-N-[cis-1-(2-phenyl-cyclohexyl)-piperidin-4-yl]-benzenesulfonamide (0.047 g, 0.090 mmol) in dichloromethane (2 ml) was cooled to −78° C. Boron tribromide 1M in dichloromethane (0.30 ml, 0.30 mmol) was added dropwise at this temperature. The mixture was then warmed to room temperature and stirred for 5 hours. The reaction was quenched with sodium hydroxyde 1N and extracted three times with dichloromethane. The combined organic phases were dried with sodium sulfate and concentrated. The residue was purified via flash chromatography on silica gel (dichloromethane/methanol/ammonia 110:10:1), yielding the title compound (0.029 mg, 63%) as an off-white solid, MS (ISP): m/e=491.3 (M+H$^+$).

EXAMPLE 158

(+/−)-N-(4-{Phenyl-[cis-1-(2-phenyl-cyclohexyl)-piperidin-4-yl]-sulfamoyl}-phenyl)-acetamide A solution of (+/−)-4-amino-N-phenyl-N-[cis-1-(2-phenyl-cyclohexyl)-piperidin-4-yl]-benzenesulfonamide (0.1 g, 0.2 mmol) in acetic acid (5 ml) was treated with acetic anhydride (1 ml) and stirred at room temperature for 1 h. The volatiles were evaporated and the residue was purified by flash chromatography on silica gel, eluting with dichloromethane/methanol/ammonia 110:10:1. The product was crystallised from hexane/ether, yielding the title compound (0.06 g, 59%) as a white solid, MS (ISP): m/e 532.5 (M+H$^+$).

EXAMPLE 159

(+/−)-N-[trans-1-(2-Hydroxy-2-phenyl-cyclohexyl)-piperidin-4-yl]-4-methoxy-N-phenyl-benzenesulfonamide The compound of the example was prepared as illustrated in scheme 5.

To a solution of 4-methoxy-N-phenyl-N-piperidin-4-yl-benzenesulfonamide (1.1 g, 3.2 mmol) in ethanol (3.5 ml) was added (+/−)-1-phenyl-7-oxa-bicyclo[4.1.0]heptane (0.180 g, 1.06 mmol). The reaction mixture was refluxed for 48 hours then cooled to room temperature and concentrated. The residue was chromatographed over silica gel (CH$_2$Cl$_2$/MeOH 49:1) to provide (+/−)-N-[trans-1-(2-hydroxy-2-phenyl-cyclohexyl)-piperidin-4-yl]-4-methoxy-N-phenyl-benzenesulfonamide (65 mg, 6%) as a white foam, MS (ISP): m/e=521.4 (M+H$^+$).

EXAMPLE 160

(+/−)-N-(4-Chloro-phenyl)-N-[trans-1-(2-hydroxy-2-phenyl-cyclohexyl)-piperidin-4-yl]-3-methoxy-benzamide The title compound, MS (ISP): m/e=519.3 (M+H$^+$), white foam, was prepared as for example 159 starting from N-(4-chloro-phenyl)-3-methoxy-N-piperidin-4-yl-benzamide.

EXAMPLE 161

(+/−)-3-Methoxy-N-(3-methyl-butyl)-N-[cis-1-(2-phenyl-cyclohexyl)-piperidin-4-yl]-benzamide The title compound, MS (ISP): m/e=463.5 (M+H$^+$), was prepared as for example 2, steps (A) to (C). Step (B) was performed using 3-methyl-butylamine, and yielded (+/−)-(3-methyl-butyl)-[cis-1-(2-phenyl-cyclohexyl)-piperidin-4-yl]-amine, which was then reacted with 3-methoxy-benzoyl chloride in step (C).

EXAMPLE 162

(+/−)-4-Methoxy-N-(3-methyl-butyl)-N-[cis-1-(2-phenyl-cyclohexyl)-piperidin-4-yl]-benzenesulfonamide The title compound, MS (ISP): m/e=499.5 (M+H$^+$), was prepared as for example 1, steps (A) to (C). Step (B) was performed using 3-methyl-butylamine, and yielded (+/−)-(3-methyl-butyl)-[cis-1-(2-phenyl-cyclohexyl)-piperidin-4-yl]-amine, which was reacted with 4-methoxy-benzensulfonyl chloride in step (C).

EXAMPLE 163

(+/−)-N-(4-Fluoro-phenyl)-N-[cis-1-(4-hydroxy-4-phenyl-tetrahydro-pyran-3-yl)-piperidin-4-yl]-4-methoxy-benzenesulfonamide The compound of the example was prepared as illustrated in scheme 2 and 6.

Preparation of N-(4-fluoro-phenyl)-4-methoxy-N-piperidin-4-yl-benzenesulfonamide. The title compound was prepared as in example 98, steps (A) to (C). Step (B) (acylation) was substituted by the following sulphonylation procedure. To a solution of 4-(4-fluoro-phenylamino)-piperidine-1-carboxylic acid tert-butyl ester (4.00 g, 13.6 mmol) in dichloromethane (60 ml) and pyridine (32 ml) was added 4-methoxybenzenesulfonyl chloride (3.40 g, 16.3 mmol). After 40 hours stirring at room temperature, the reaction mixture was diluted with ethyl acetate (80 ml), washed with chlorhydric acid (2×50 ml, 0.5 N) and with saturated sodium hydrogencarbonate (50 ml), dried over sodium sulphate, filtered and concentrated in vacuo. The residue was taken in ether to provide a precipitate. Filtration led to 4-[(4-fluoro-phenyl)-(4-methoxy-benzenesulfonyl)-amino]-piperidine-1-carboxylic acid tert-butyl ester (4.70 g, 74%) as a off white solid, MS (ISP): m/e=465.2 (M+H$^+$).

(A and B) Preparation of (+/−)-N-(4-fluoro-phenyl)-4-methoxy-N-[1-(4-oxo-tetrahydro-pyran-3-yl)-piperidin-4-yl]-benzenesulfonamide and (+/−)-N-(4-fluoro-phenyl)-4-methoxy-N-[1-(3-oxo-tetrahydro-pyran-4-yl)-piperidin-4-yl]-benzenesulfonamide. To a solution of N-(4-fluoro-phenyl)-4-methoxy-N-piperidin-4-yl-benzenesulfonamide (7.60 g, 20.8 mmol) in ethanol (30 ml) was added rac-3,7-dioxa-bicyclo[4.1.0]heptane (2.50 g, 25.0 mmol). The reaction mixture was refluxed overnight, concentrated in vacuo and dissolved in dichloromethane (60 ml), dimethylsulfoxide (30 ml) and triethylamine (4.93 ml). The reaction mixture was cooled to 0° C. and a solution of sulfur trioxide-pyridine complex (7.47 g, 21.1 mmol) in dimethylsulfoxide (30 ml) was added dropwise. After 2.5 hours stirring at RT, the reaction mixture was poured into water and dichloromethane. The aqueous phase was extracted with dichloromethane, the combined organic layers were dried over sodium sulphate, filtered and concentrated in vacuo. The residue was chromatographed over silica gel (heptane-ethylacetate 1:1) to provide N-(4-fluoro-phenyl)-4-methoxy-N-[1-(4-oxo-tetrahydro-pyran-3-yl)-piperidin-4-yl]-benzenesulfonamide (1.45 g, 15%, first eluting compound) as a yellow oil, MS (ISP): m/e=463.2 (M+H$^+$) and N-(4-fluoro-phenyl)-4-methoxy-N-[1-(3-oxo-tetrahydro-pyran-4-yl)-piperidin-4-yl]-benzenesulfonamide (0.120 g, 1.2%, second eluting compound) as a yellow oil, MS (ISP): m/e=463.2 (M+H$^+$).

(F) Preparation of (+/−)-N-(4-fluoro-phenyl)-N-[cis-1-(4-hydroxy-4-phenyl-tetrahydro-pyran-3-yl)-piperidin-4-yl]-4-methoxy-benzenesulfonamide. To a −78° C. solution of (+/−)-N-(4-fluoro-phenyl)-4-methoxy-N-[1-(4-oxo-tetrahydro-pyran-3-yl)-piperidin-4-yl]-benzenesulfonamide (0.30 g, 0.65 mmol) in tetrahydrofuran (5 ml) was added phenyl lithium (1.7 M solution in cyclohexane/ether, 0.84 ml, 1.4 mmol). After 90 min. stirring at −78° C., the reaction mixture was quenched with saturated ammonium chloride (5 ml) and the aqueous phase was extracted with ethyl acetate. The combined organic layers were dried over sodium sulphate, filtered and concentrated in vacuo. The residue was chromatographed over silica gel (heptane/ethylacetate 7:3) to provide (+/−)-N-(4-fluoro-phenyl)-N-[cis-1-(4-hydroxy-4-phenyl-tetrahydro-pyran-3-yl)-piperidin-4-yl]-4-methoxy-benzenesulfonamide (0.040 g, 12%) as a light yellow solid, MS (ISP): m/e=541.3 (M+H$^{3O}$).

EXAMPLE 164

(+/−)-N-(4-Fluoro-phenyl)-N-[cis-1-(3-hydroxy-3-phenyl-tetrahydro-pyran-4-yl)-piperidin-4-yl]-4-methoxy-benzenesulfonamide The title compound of the example, MS (ISP): m/e=541.3 (M+H$^+$), yellow solid, was prepared as for example 163, step (B), starting from N-(4-fluoro-phenyl)-4-methoxy-N-[1-(3-oxo-tetrahydro-pyran-4-yl)-piperidin-4-yl]-benzenesulfonamide.

EXAMPLE 165

(+/−)-N-(4-Fluoro-phenyl)-N-[cis-1-(4-hydroxy-4-phenyl-tetrahydro-pyran-3-yl)-piperidin-4-yl]-3-methoxy-benzamide The title compound of the example, MS (ISP): m/e=505.3 (M+H$^+$), white foam, was prepared as for example 163, steps (A) to (F). N-(4-fluoro-phenyl)-3-methoxy-N-piperidin-4-yl-benzamide was used in step (A): oxidation provided (+/−)-N-(4-fluoro-phenyl)-3-methoxy-N-[1-(4-oxo-tetrahydro-pyran-3-yl)-piperidin-4-yl]-benzamide, which was reacted with phenyl lithium in step (F).

EXAMPLE 166

(+/−)-N-Phenyl-N-[cis-1-(2-phenyl-cyclohexyl)-piperidin-4-yl]-nicotinamide

The title compound, MS (ISP): m/e=440.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with nicotinoyl chloride in step (C).

EXAMPLE 167

(+/−)-Furan-2-carboxylic acid phenyl-[cis-1-(2-phenyl-cyclohexyl)-piperidin-4-yl]-amide The title compound, MS (ISP): m/e=429.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with furan-2-carbonyl chloride in step (C).

EXAMPLE 168

(+/−)-Thiophene-2-carboxylic acid phenyl-[cis-1-(2-phenyl-cyclohexyl)-piperidin-4-yl]-amide The title compound, MS (ISP): m/e=445.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted thiophene-2-carbonyl chloride in step (C).

EXAMPLE 169

(+/−)-Thiophene-3-carboxylic acid phenyl-[cis-1-(2-phenyl-cyclohexyl)-piperidin-4-yl]-amide The title compound, MS (ISP): m/e=445.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with thiophene-3-carbonyl chloride in step (C).

EXAMPLE 170

(+/−)-Isoxazole-5-carboxylic acid phenyl-[cis-1-(2-phenyl-cyclohexyl)-piperidin-4-yl]-amide The title compound, MS (ISP): m/e=430.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with isoxazole-5-carbonyl chloride in step (C).

EXAMPLE 171

(+/−)-5-Methyl-isoxazole-3-carboxylic acid phenyl-[cis-1-(2-phenyl-cyclohexyl)-piperidin-4-yl]-amide The title compound, MS (ISP): m/e=444.4 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with 5-methyl-isoxazole-3-carbonyl chloride in step (C).

EXAMPLE 172

(+/−)-2,5-Dimethyl-2H-pyrazole-3-carboxylic acid phenyl-[cis-1-(2-phenyl-cyclohexyl)-piperidin-4-yl]-amide The title compound, MS (ISP): m/e=457.5 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with 2,5-dimethyl-2H-pyrazole-3-carbonyl chloride in step (C).

EXAMPLE 173

(+/−)-Pyrazine-2-carboxylic acid phenyl-[cis-1-(2-phenyl-cyclohexyl)-piperidin-4-yl]-amide The title compound, MS (ISP): m/e=441.7 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with pyrazine-2-carbonyl chloride in step (C).

EXAMPLE 174

(+/−)-2-Methyl-N-phenyl-N-[cis-1-(2-phenyl-cyclohexyl)-piperidin-4-yl]-benzamide The title compound, MS (ISP): m/e=453.8 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with 2-methyl-benzoyl chloride in step (C).

EXAMPLE 175

(+/−)-Benzo[1,3]dioxole-5-carboxylic acid phenyl-[cis-1-(2-phenyl-cyclohexyl)-piperidin-4-yl]-amide The title compound, MS (ISP): m/e=483.8 (M+H$^+$), was prepared as for example 2, steps (A) to (C). Step (B) was performed using aniline, and yielded (+/−)-phenyl-[cis-1-(2-phenyl-cyclohexyl)-piperidin-4-yl]-amine, which was reacted with benzo[1,3]dioxole-5-carbonyl chloride in step (C).

EXAMPLE 176

(+/−)-N-(3,5-Dimethyl-phenyl)-N-[cis-1-(2-phenyl-cyclohexyl)-piperidin-4-yl]-benzamide The title compound, MS (ISP): m/e=467.4 (M+H$^+$), was prepared as for example 2, steps (A) to (C). Step (B) was performed using 3,5-dimethylaniline, and yielded (+/−)-(3,5-dimethyl-phenyl)-[cis-1-(2-phenyl-cyclohexyl)-piperidin-4-yl]-amine, which was reacted with benzoyl chloride in step (C).

EXAMPLE 177

(+/−)-4-Dimethylamino-N-(3,5-dimethyl-phenyl)-N-[cis-1-(2-phenyl-cyclohexyl)-piperidin-4-yl]-benzamide The title compound, MS (ISP): m/e=510.3 (M+H$^+$), was prepared as for example 2, steps (A) to (C). Step (B) was performed using 3,5-dimethylaniline, and yielded (+/−)-(3,5-dimethyl-phenyl)-[cis-1-(2-phenyl-cyclohexyl)-piperidin-4-yl]-amine, which was reacted with 4-dimethylamino benzoyl chloride in step (C).

EXAMPLE 178

(+/−)-3-Methoxy-N-phenethyl-N-[cis-1-(2-phenyl-cyclohexyl)-piperidin-4-yl]-benzamide The title compound, MS (ISP): m/e=497.4 (M+H$^+$), was prepared as for example 2, steps (A) to (C). Step (B) was performed using phenethylamine, and yielded (+/−)-phenethyl-[cis-1-(2-phenyl-cyclohexyl)-piperidin-4-yl]-amine, which was reacted with 3-methoxy benzoyl chloride in step (C).

EXAMPLE 179

(+/−)-3,4-Dimethoxy-N-phenethyl-N-[cis-1-(2-phenyl-cyclohexyl)-piperidin-4-yl]-benzamide The title compound, MS (ISP): m/e=527.3 (M+H$^+$), was prepared as for example 2, steps (A) to (C). Step (B) was performed using phenethylamine, and yielded (+/−)-phenethyl-[cis-1-(2-phenyl-cyclohexyl)-piperidin-4-yl]-amine, which was reacted with 3,4-dimethoxy benzoyl chloride in step (C).

EXAMPLE 180

(+/−)-N-Benzyl-4-dimethylamino-N-[cis-1-(2-phenyl-cyclohexyl)-piperidin-4-yl]-benzamide The title compound, MS (ISP): m/e=496.4 (M+H$^+$), was prepared as for example 2, steps (A) to (C). Step (B) was performed using benzylamine, and yielded (+/−)-benzyl-[cis-1-(2-phenyl-cyclohexyl)-piperidin-4-yl]-amine, which was reacted with 4-dimethylamino benzoyl chloride in step (C).

EXAMPLE 181

(+/−)-N-Benzyl-3,4-dimethoxy-N-[cis-1-(2-phenyl-cyclohexyl)-piperidin-4-yl]-benzamide The title compound, MS (ISP): m/e=513.3 (M+H$^+$), was prepared as for example 2, steps (A) to (C). Step (B) was performed using benzylamine, and yielded (+/−)-benzyl-[cis-1-(2-phenyl-cyclohexyl)-piperidin-4-yl]-amine, which was reacted with 3,4-dimethoxy benzoyl chloride in step (C).

EXAMPLE 182

(+/−)-N-(3,5-Difluoro-phenyl)-2,5-difluoro-N-[cis-1-(2-phenyl-cyclohexyl)-piperidin-4-yl]-benzamide The title compound, MS (ISP): m/e=511.2 (M+H$^+$), was prepared as for example 2, steps (A) to (C). Step (B) was performed using 3,5-difluoroaniline, and yielded (+/−)-(3,5-difluoro-phenyl)-[cis-1-(2-phenyl-cyclohexyl)-piperidin-4-yl]-amine, which was reacted with 2,5-difluoro benzoyl chloride in step (C).

EXAMPLE 183

N-(3,5-Difluoro-phenyl)-2-methyl-N-[cis-1-(2-phenyl-cyclohexyl)-piperidin-4-yl]-benzamide The title compound, MS (ISP): m/e=489.3 (M+H$^+$), was prepared as for example 2, steps (A) to (C). Step (B) was performed using 3,5-difluoroaniline, and yielded (+/−)-(3,5-difluoro-phenyl)-[cis-1-(2-phenyl-cyclohexyl)-piperidin-4-yl]-amine, which was reacted with 2-methyl-benzoyl chloride in step (C).

EXAMPLE 184

(+/−)-2-Ethyl-5-methyl-2H-pyrazole-3-carboxylic acid (3,5-difluoro-phenyl)-[cis-1-(2-phenyl-cyclohexyl)-piperidin-4-yl]-amide The title compound, MS (ISP): m/e=507.2 (M+H$^+$), was prepared as for example 2, steps (A) to (C). Step (B) was performed using 3,5-difluoroaniline, and yielded (+/−)-(3,5-difluoro-phenyl)-[cis-1-(2-phenyl-cyclohexyl)-piperidin-4-yl]-amine, which was reacted with 2-ethyl-5-methyl-2H-pyrazole-3-carbonyl chloride in step (C).

EXAMPLE 185

(+/−)-Benzo[1,3]dioxole-5-carboxylic acid (4-chloro-phenyl)-[cis-1-(2-phenyl-cyclohexyl)-piperidin-4-yl]-amide The title compound, MS (ISP): m/e=517.2 (M+H$^+$), was prepared as for example 2, steps (A) to (C). Step (B) was performed using 4-chloroaniline, and yielded (+/−)-(4-chloro-phenyl)-[cis-1-(2-phenyl-cyclohexyl)-piperidin-4-yl]-amine, which was reacted with benzo[1,3]dioxole-5-carbonyl chloride in step (C).

EXAMPLE 186

(+/−)-Benzo[1,3]dioxole-5-carboxylic acid[cis-1-(2-phenyl-cyclohexyl)-piperidin-4-yl]-p-tolyl-amide The title compound, MS (ISP): m/e=497.3 (M+H$^+$), was prepared as for example 2, steps (A) to (C). Step (B) was performed using p-tolyl-amine, and yielded (+/−)-[cis-1-(2-phenyl-cyclohexyl)-piperidin-4-yl]-p-tolyl-amine, which was reacted with benzo[1,3]dioxole-5-carbonyl chloride in step (C).

EXAMPLE 187

(+/−)-4-Cyano-N-[cis-1-(2-phenyl-cyclohexyl)-piperidin-4-yl]-N-p-tolyl-benzamide The title compound, MS (ISP): m/e=478.4 (M+H$^+$), was prepared as for example 2, steps (A) to (C). Step (B) was performed using p-tolyl-amine, and yielded (+/−)-[cis-1-(2-phenyl-cyclohexyl)-piperidin-4-yl]-p-tolyl-amine, which was reacted with 4-cyano-benzoyl chloride in step (C).

EXAMPLE 188

(+/−)-Benzo[b]thiophene-3-carboxylic acid[cis-1-(2-phenyl-cyclohexyl)-piperidin-4-yl]-p-tolyl-amide The title compound, MS (ISP): m/e=509.3 (M+H$^+$), was prepared as for example 2, steps (A) to (C). Step (B) was performed using p-tolyl-amine, and yielded (+/−)-[cis-1-(2-phenyl-cyclohexyl)-piperidin-4-yl]-p-tolyl-amine, which was reacted with benzo[b]thiophene-3-carbonyl chloride in step (C).

EXAMPLE 189

(+/−)-N-[cis-1-(2-Phenyl-cyclohexyl)-piperidin-4-yl]-N-p-tolyl-isonicotinamide

The title compound, MS (ISP): m/e=454.2 (M+H⁺), was prepared as for example 2, steps (A) to (C). Step (B) was performed using p-tolyl-amine, and yielded (+/−)-[cis-1-(2-phenyl-cyclohexyl)-piperidin-4-yl]-p-tolyl-amine, which was reacted with isonicotinoyl chloride in step (C).

EXAMPLE 190

(+/−)-4-Cyano-N-(3-methoxy-phenyl)-N-[cis-1-(2-phenyl-cyclohexyl)-piperidin-4-yl]-benzamide The title compound, MS (ISP): m/e=494.3 (M+H⁺), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 4-cyano-benzoyl chloride in step (C).

EXAMPLE 191

(+/−)-N-(3-Methoxy-phenyl)-N-[cis-1-(2-phenyl-cyclohexyl)-piperidin-4-yl]-4-pyrazol-1-yl-benzamide The title compound, MS (ISP): m/e=535.3 (M+H⁺), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 4-pyrazol-1-yl-benzoyl chloride in step (C).

EXAMPLE 192

(+/−)-1-Methyl-1H-benzotriazole-5-carboxylic acid (3-methoxy-phenyl)-[cis-1-(2-phenyl-cyclohexyl)-piperidin-4-yl]-amide The title compound, MS (ISP): m/e=524.3 (M+H⁺), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 1-methyl-1H-benzotriazole-5-carbonyl chloride in step (C).

EXAMPLE 193

(+/−)-5-Chloro-1-methyl-1H-pyrazole-4-carboxylic acid (3-methoxy-phenyl)-[cis-1-(2-phenyl-cyclohexyl)-piperidin-4-yl]-amide The title compound, MS (ISP): m/e=507.3 (M+H⁺), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 5-chloro-1-methyl-1H-pyrazole-4-carbonyl chloride in step (C).

EXAMPLE 194

(+/−)-3,4-Dimethoxy-N-(3-methoxy-phenyl)-N-[cis-1-(2-phenyl-cyclohexyl)-piperidin-4-yl]-benzamide The title compound, MS (ISP): m/e=529.3 (M+H⁺), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 3,4-dimethoxy-benzoyl chloride in step (C).

EXAMPLE 195

(+/−)-2-Ethyl-5-methyl-2H-pyrazole-3-carboxylic acid (3-methoxy-phenyl)-[cis-1-(2-phenyl-cyclohexyl)-piperidin-4-yl]-amide The title compound, MS (ISP): m/e=501.3 (M+H⁺), was prepared as for example 2, steps (A) to (C). Step (B) was performed using 3-methoxy-aniline, and yielded (+/−)-(3-methoxy-phenyl)-[cis-1-(2-phenyl-cyclohexyl)-piperidin-4-yl]-amine, which was reacted with 2-ethyl-5-methyl-2H-pyrazole-3-carbonyl chloride in step (C).

EXAMPLE 196

(+/−)-2-Methyl-N-[cis-1-(2-phenyl-cyclohexyl)-piperidin-4-yl]-N-(4-trifluoromethoxy-phenyl)-benzamide The title compound, MS (ISP): m/e=537.3 (M+H⁺), was prepared as for example 2, steps (A) to (C). Step (B) was performed using 4-trifluoromethoxy-aniline, and yielded (+/−)-[cis-1-(2-phenyl-cyclohexyl)-piperidin-4-yl]-(4-trifluoromethoxy-phenyl)-amine, which was reacted with 2-methyl-benzoyl chloride in step (C).

EXAMPLE 197

(+/−)-N-[cis-1-(2-Phenyl-cyclohexyl)-piperidin-4-yl]-N-(4-trifluoromethoxy-phenyl)-nicotinamide The title compound, MS (ISP): m/e=524.2 (M+H⁺), was prepared as for example 2, steps (A) to (C). Step (B) was performed using 4-trifluoromethoxy-aniline, and yielded (+/−)-[cis-1-(2-phenyl-cyclohexyl)-piperidin-4-yl]-(4-trifluoromethoxy-phenyl)-amine, which was reacted with nicotinoyl chloride in step (C).

EXAMPLE 198

(+/−)-2-Ethyl-5-methyl-2H-pyrazole-3-carboxylic acid[cis-1-(2-phenyl-cyclohexyl)-piperidin-4-yl]-(4-trifluoromethoxy-phenyl)-amide The title compound, MS (ISP): m/e=555.3 (M+H⁺), was prepared as for example 2, steps (A) to (C). Step (B) was performed using 4-trifluoromethoxy-aniline, and yielded (+/−)-[cis-1-(2-phenyl-cyclohexyl)-piperidin-4-yl]-(4-trifluoromethoxy-phenyl)-amine, which was reacted with 2-ethyl-5-methyl-2H-pyrazole-3-carbonyl chloride in step (C).

EXAMPLE 199

(+/−)-Naphthalene-2-carboxylic acid (2-chloro-phenyl)-[cis-1-(2-phenyl-cyclohexyl)-piperidin-4-yl]-amide The title compound, MS (ISP): m/e=523.3 (M+H$^+$), was prepared as for example 2, steps (A) to (C). Step (B) was performed using 2-chloro-aniline, and yielded (+/−)-(2-chloro-phenyl)-[cis-1-(2-phenyl-cyclohexyl)-piperidin-4-yl]-amine, which was reacted with naphthalene-2-carbonyl chloride in step (C).

EXAMPLE 200

(+/−)-N-(2-Chloro-phenyl)-2-methyl-N-[cis-1-(2-phenyl-cyclohexyl)-piperidin-4-yl]-benzamide The title compound, MS (ISP): m/e=487.3 (M+H$^+$), was prepared as for example 2, steps (A) to (C). Step (B) was performed using 2-chloro-aniline, and yielded (+/−)-(2-chloro-phenyl)-[cis-1-(2-phenyl-cyclohexyl)-piperidin-4-yl]-amine, which was reacted with 2-methyl-benzoyl chloride in step (C).

EXAMPLE 201

(+/−)-Benzo[1,3]dioxole-5-carboxylic acid (3-dimethylamino-phenyl)-[cis-1-(2-phenyl-cyclohexyl)-piperidin-4-yl]-amide The title compound, MS (ISP): m/e=526.3 (M+H$^+$), was prepared as for example 2, steps (A) to (C). Step (B) was performed using 3-dimethylamino-aniline, and yielded (+/−)-(3-dimethylamino-phenyl)-[cis-1-(2-phenyl-cyclohexyl)-piperidin-4-yl]-amine, which was reacted with benzo[1,3]dioxole-5-carbonyl chloride in step (C).

EXAMPLE 202

(+/−)-N-(3-Dimethylamino-phenyl)-3,4-dimethoxy-N-[cis-1-(2-phenyl-cyclohexyl)-piperidin-4-yl]-benzamide The title compound, MS (ISP): m/e=542.3 (M+H$^+$), was prepared as for example 2, steps (A) to (C). Step (B) was performed using 3-dimethylamino-aniline, and yielded (+/−)-(3-dimethylamino-phenyl)-[cis-1-(2-phenyl-cyclohexyl)-piperidin-4-yl]-amine, which was reacted with 3,4-dimethoxybenzoyl chloride in step (C).

EXAMPLE 203

(+/−)-5-Chloro-N-(3-dimethylamino-phenyl)-2-fluoro-N-[cis-1-(2-phenyl-cyclohexyl)-piperidin-4-yl]-benzamide The title compound, MS (ISP): m/e=534.7 (M+H$^+$), was prepared as for example 2, steps (A) to (C). Step (B) was performed using 3-dimethylamino-aniline, and yielded (+/−)-(3-dimethylamino-phenyl)-[cis-(1-(2-phenyl-cyclohexyl)-piperidin-4-yl]-amine, which was reacted with 5-chloro-2-fluoro-benzoyl chloride in step (C).

EXAMPLE 204

(+/−)-5-Chloro-1-methyl-1H-pyrazole-4-carboxylic acid (3-dimethylamino-phenyl)-[cis-1-(2-phenyl-cyclohexyl)-piperidin-4-yl]-amide The title compound, MS (ISP): m/e=520.3 (M+H$^+$), was prepared as for example 2, steps (A) to (C). Step (B) was performed using 3-dimethylamino-aniline, and yielded (+/−)-3-dimethylamino-phenyl)-[cis-(1-(2-phenyl-cyclohexyl)-piperidin-4-yl]-amine, which was reacted with 5-chloro-1-methyl-1H-pyrazole-4-carbonyl chloride in step (C).

EXAMPLE 205

(+/−)-N-(3-Acetylamino-phenyl)-2-methyl-N-[cis-1-(2-phenyl-cyclohexyl)-piperidin-4-yl]-3-trifluoromethyl-benzamide The title compound, MS (ISP): m/e=578.9 (M+H$^+$), was prepared as for example 2, steps (A) to (C). Step (B) was performed using 3-acetylamino-aniline, and yielded (+/−)-N-{3-[cis-1-(2-phenyl-cyclohexyl)-piperidin-4-ylamino]-phenyl}-acetamide, which was reacted with 2-methyl-3-trifluoromethyl-benzoyl chloride in step (C).

EXAMPLE 206

(+/−)-Pyrazine-2-carboxylic acid (4-methoxy-phenyl)-[cis-1-(2-phenyl-cyclohexyl)-piperidin-4-yl]-amide The title compound, MS (ISP): m/e=471.8 (M+H$^+$), was prepared as for example 2, steps (A) to (C). Step (B) was performed using 4-methoxy-aniline, and yielded (+/−)-(4-methoxy-phenyl)-[cis-1-(2-phenyl-cyclohexyl)-piperidin-4-yl]-amine, which was reacted with pyrazine-2-carbonyl chloride in step (C).

EXAMPLE 207

(+/−)-Naphthalene-2-carboxylic acid (2-acetylamino-phenyl)-[cis-1-(2-phenyl-cyclohexyl)-piperidin-4-yl]-amide The title compound, MS (ISP): m/e=546.8 (M+H$^+$), was prepared as for example 2, steps (A) to (C). Step (B) was performed using 2-acetylamino-aniline, and yielded (+/−)-N-{2-[cis-1-(2-Phenyl-cyclohexyl)-piperidin-4-ylamino]-phenyl}-acetamide, which was reacted with naphthalene-2-carbonyl chloride in step (C).

EXAMPLE 208

(+/−)-Isoxazole-5-carboxylic acid (2-fluoro-4-trifluoromethyl-phenyl)-[1-((1S,2S)-2-phenyl-cyclohexyl)-piperidin-4-yl]-amide The title compound, MS (ISP): m/e=516.1 (M+H$^+$), was prepared as for example 2, steps (A) to (C). Step (B) was performed using 2-fluoro-4-trifluoromethyl-aniline, and yielded (+/−)-(2-fluoro-4-trifluoro-phenyl)-[cis-1-(2-phenyl-cyclohexyl)-piperidin-4-yl]-amine, which was reacted with isoxazole-5-carbonyl chloride in step (C).

EXAMPLE 209

(+/−)-N-[cis-1-(2-Phenyl-cyclohexyl)-piperidin-4-yl]-N-pyridin-2-yl-benzamide (A) Reductive amination to (+/−)-[cis-1-(2-phenyl-cyclohexyl)-piperidin-4-yl]-amine. A solution of (+/−)-cis-1-(2-phenyl-cyclohexyl)-piperidin-4-one (4.67 g, 18.14 mmol) and ammonium formiate (10.60 g, 168.1 mmol) in technical methanol (48 ml) and water (5.1 ml) was treated with Pd/C (10%, 2.11 g). The resulting suspension was stirred under an argon atmosphere for 18 h. The catalyst was filtered washing with methanol and the filtrate was evaporated, yielding crude (+/−)-[cis-1-(2-phenyl-cyclohexyl)-piperidin-4-yl]-amine (4.07 g, 87%) as a colorless liquid, MS (ISP): m/e=259.3 (M+H$^+$).

(B) Coupling of (+/−)-[cis-1-(2-phenyl-cyclohexyl)-piperidin-4-yl]-amine with 2-bromo-pyridine to yield (+/−)-[cis-1-(2-phenyl-cyclohexyl)-piperidin-4-yl]-pyridin-2-yl-amine. A suspension of (+/−)-[cis-1-(2-phenyl-cyclohexyl)-piperidin-4-yl]-amine (1.00 g, 3.83 mmol) in toluene (30 ml) was degassed with a flow of argon for 10 minutes. Palladium (II) acetate (27.0 mg, 0.12 mmol), rac-2,2'-bis(diphenylphosphino)-1,1'-binaphtyl (BINAP, 71.6 mg, 0.11 mmol), sodium tert-butoxide (0.45 g, 4.65 mmol) and 2-bromopyridine (0.49 g, 3.13 mmol) were added under argon. The flask was sealed and warmed to 70° C. for 3 hours. The mixture was diluted with ethyl acetate (30 ml) and diethyl ether (30 ml) and washed three times with saturated sodium chloride solution. The organic phase was dried with sodium sulphate and evaporated, yielding an orange oil. Purification was achieved by flash chromatography (dichloromethane/methanol/25% NH$_3$ 90:10:1). The title amine (0.326 g, 25%) was obtained as a yellow oil, MS (ISP): m/e 336.3 (M+H$^+$).

(C) Acylation to (+/−)-N-[cis-1-(2-Phenyl-cyclohexyl)-piperidin-4-yl]-N-pyridin-2-yl-benzamide. To an aliquot of polystyrene-bound 2-tert-butylimino-2-diethylamino-1,3-dimethyl-perhydro-1,3,2-diazaphosphorine (PS-BEMP, 2.2 mmol/g, 0.120 g, 0.264 mmol) was added a solution of (+/−)-[cis-1-(2-phenyl-cyclohexyl)-piperidin-4-yl]-pyridin-2-yl-amine in THF (0.15 M, 0.6 ml, 0.088 mmol) and a solution of benzoyl chloride in THF (1.17 M, 0.3 ml, 0.35 mmol). The mixture was shaken at room temperature for 18 hours, then filtered washing with THF. The filtrate is injected into a preparative HPLC (Column: YMC Combiprep C18, CCASS05-052OWT, 50×20 mm I.D., S-5 μm 120 Å; Flux: 30 ml/min; Program: 0–0.5' 20% acetonitrile in water+ 0.05% HCO$_2$H; 95% @ 2.5'; 95% @ 4.75'; 20% @ 4.80°; program end @ 5 min). The title compound, MS (ISP): m/e=440.4 (M+H$^+$), is obtained as a white solid (5.8 mg, 15%).

EXAMPLE 210

(+/−)-5-Methyl-isoxazole-3-carboxylic acid[cis-1-(2-phenyl-cyclohexyl)-piperidin-4-yl]-pyridin-2-yl-amide The title compound, MS (ISP): m/e=445.4 (M+H$^+$), was prepared as for example 209, steps (A) to (C). Step (B) was performed using 2-bromo-pyridine and yielded (+/−)-[cis-1-(2-phenyl-cyclohexyl)-piperidin-4-yl]-pyridin-2-yl-amine, which was reacted with 5-methyl-isoxazole-3-carbonyl chloride in step (C).

EXAMPLE 211

(+/−)-N-[cis-1-(2-Phenyl-cyclohexyl)-piperidin-4-yl]-N-pyridin-3-yl-benzamide

The title compound, MS (ISP): m/e=440.4 (M+H$^+$), was prepared as for example 209, steps (A) to (C). Step (B) was performed using 3-bromo-pyridine as follows: A suspension of (+/−)-[cis-1-(2-phenyl-cyclohexyl)-piperidin-4-yl]-amine (1.00 g, 3.88 mmol) in toluene (30 ml) was degassed with a flow of argon for 10 minutes. Tris-(dibenzylideneacetone)dipalladium chloroform complex (124 mg, 0.12 mmol), rac-2,2'-bis(diphenylphosphino)-1,1'-binaphtyl (BINAP, 76.0 mg, 0.12 mmol), sodium tert-butoxide (0.470 g, 4.89 mmol) and 3-bromopyridine (0.483 g, 3.06 mmol) were added under argon. The flask was sealed and warmed to 70° C. for 3 hours. The mixture was diluted with ethyl acetate (30 ml) and diethyl ether (30 ml) and washed three times with saturated sodium chloride solution. The organic phase was dried with sodium sulphate and evaporated, yielding a red oil. Purification was achieved by flash chromatography (dichloromethane/methanol/25% NH$_3$ 90:10:1). (+/−)-[cis-1-(2-Phenyl-cyclohexyl)-piperidin-4-yl]-pyridin-3-yl-amine (0.260 g, 20%) was obtained as an orange foam, MS (ISP): m/e=336.3 (M+H$^+$). This was reacted with benzoyl chloride in step (C).

EXAMPLE 212

(+/−)-5-Methyl-isoxazole-3-carboxylic acid[cis-1-(2-phenyl-cyclohexyl)-piperidin-4-yl]-pyridin-3-yl-amide The title compound, MS (ISP): m/e=445.4 (M+H$^+$), was prepared as for example 209, steps (A) to (C). Step (B) was performed using 3-bromo-pyridine and yielded (+/−)-[cis-1-(2-phenyl-cyclohexyl)-piperidin-4-yl]-pyridin-3-yl-amine, which was reacted with 5-methyl-isoxazole-3-carbonyl chloride in step (C).

EXAMPLE 213

(+/−)-N-[cis-1-(2-Phenyl-cyclohexyl)-piperidin-4-yl]-N-pyridin-4-yl-benzamide

The title compound, MS (ISP): m/e=440.4 (M+H$^+$), was prepared as for example 209, steps (A) to (C). Step (B) was performed using 4-bromo-pyridine as follows: A suspension of (+/−)-[cis-1-(2-phenyl-cyclohexyl)-piperidin-4-yl]-amine (0.303 g, 1.17 mmol) in toluene (10 ml) was degassed with a flow of argon for 10 minutes. Palladium(II) acetate (8.0 mg, 0.036 mmol), rac-2,2'-bis(diphenylphosphino)-1,1'-binaphtyl (BINAP, 23.0 mg, 0.037 mmol), sodium tert-butoxide (0.280 g, 2.91 mmol) and 4-bromopyridine hydrochloride (0.194 g, 1.00 mmol) were added under argon. The flask was sealed and warmed to 70° C. for 3 hours. The mixture was diluted with ethyl acetate (10 ml) and diethyl ether (10 ml) and washed three times with saturated sodium chloride solution. The organic phase was dried with sodium sulphate and evaporated, yielding an orange oil. Purification was achieved by flash chromatography (dichloromethane/methanol/25% NH$_3$ 65:10:1). (+/−)-[cis-1-(2-Phenyl-cyclohexyl)-piperidin-4-yl]-pyridin-4-yl-amine (0.187 g, 47%) was obtained as a light yellow foam, MS (ISP): m/e=336.3 (M+H$^+$). This was reacted with benzoyl chloride in step (C).

EXAMPLE 214

(+/−)-5-Methyl-isoxazole-3-carboxylic acid[cis-1-(2-phenyl-cyclohexyl)-piperidin-4-yl]-pyrimidin-5-yl-amide The title compound, MS (ISP): m/e=446.4 (M+H$^+$), was prepared as for example 209, steps (A) to (C). Step (B) was performed using 5-bromo-pyrimidine as follows: A suspension of (+/−)-[cis-1-(2-phenyl-cyclohexyl)-piperidin-4-yl]-amine (1.46 g, 5.65 mmol) in toluene (35 ml) was degassed with a flow of argon for 10 minutes. Tris-(dibenzylideneacetone)dipalladium chloroform complex (179 mg, 0.17 mmol), rac-2,2'-bis(diphenylphosphino)-1,1'-binaphtyl (BINAP, 108.0 mg, 0.17 mmol), sodium tert-butoxide (0.660 g, 6.87 mmol) and 5-bromopyrimidine (0.720 g, 4.53 mmol) were added under argon. The flask was sealed and warmed to 70° C. for 3 hours. The mixture was diluted with ethyl acetate (30 ml) and diethyl ether (30 ml) and washed three times with saturated sodium chloride solution. The organic phase was dried with sodium sulphate and evaporated, yielding a red oil. Purification was achieved by flash chromatography (dichloromethane/methanol/25% NH3 90:10:1). (+/−)-[cis-1-(2-Phenyl-cyclohexyl)-piperidin-4-yl]-pyrimidin-5-yl-amine (0.392 g, 20.6%) was obtained as an orange foam, MS (ISP): m/e=337.3 (M+H$^+$). This was reacted with 5-methyl-isoxazole-3-carbonyl chloride in step (C).

Tablet Formulation (Wet Granulation)

| Item | Ingredients | 5 mg | 25 mg | 100 mg | 500 mg |
|---|---|---|---|---|---|
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredients | 5 mg | 25 mg | 100 mg | 500 mg |
|---|---|---|---|---|---|
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The invention claimed is:

1. A compound of formula

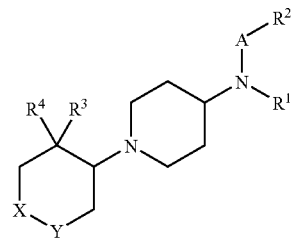

I wherein
R$^1$ is lower alkyl, —(CH$_2$)$_n$-aryl, unsubstituted or substituted by one or two substituents selected from the group consisting of lower alkyl, lower alkoxy, —OCF$_3$, halogen, —NR'R" and trifluoromethyl;
R$^2$ is lower alkyl, —(CH$_2$)$_n$-aryl, unsubstituted or substituted by one or two substituents selected from the group consisting of lower alkyl, lower alkoxy, halogen, trifluoromethyl, nitro, cyano, —NR'R", and hydroxy;
R$^3$ is aryl, unsubstituted or substituted by halogen or lower alkyl;
R$^4$ is hydrogen or hydroxy;
A is —S(O)$_2$— or —C(O)—;
X and Y are each —CH$_2$—;
R' and R" are each independently selected from the group consisting of hydrogen, lower alkyl and —C(O)-lower alkyl;
n is 0, 1 or 2;
or a pharmaceutically acceptable acid addition salt thereof.

2. A compound of formula

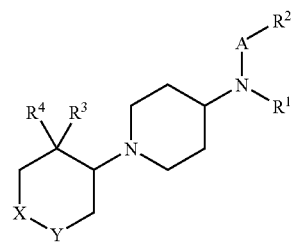

IA in accordance with claim 1, wherein
R$^1$ is lower alkyl, benzyl or is phenyl, unsubstituted or substituted by one or two substituents selected from the group consisting of lower alkyl, lower alkoxy, halogen and trifluoromethyl;
R$^2$ is lower alkyl, benzyl, or is phenyl, unsubstituted or substituted by one or two substituents selected from the group consisting of lower alkyl, lower alkoxy, halogen, trifluoromethyl, nitro, amino, hydroxy and —NHC(O)-lower alkyl;
R$^3$ is phenyl, unsubstituted or substituted by halogen or lower alkyl;
R$^4$ is hydrogen or hydroxy;
A is —S(O)$_2$— or —C(O)—;
X and Y are each —CH$_2$—;
or a pharmaceutically acceptable acid addition salt thereof.

3. A compound according to claim 1, wherein A is S(O)$_2$.

4. A compound according to claim 3, wherein R$^3$ is phenyl, unsubstituted or substituted by halogen or lower alkyl.

5. A compound according to claim 4, wherein R³ is unsubstituted phenyl.

6. A compound according to claim 5, wherein R⁴ is hydrogen.

7. A compound according to claim 6, selected from the group consisting of
(+/−)-3,4-dichloro-N-phenyl-N-[cis-1-(2-phenyl-cyclohexyl)-piperidin-4-yl]-benzenesulfonamide,
(+/−)-4-methoxy-N-(3-methoxy-phenyl)-N-[cis-1-(2-phenyl-cyclohexyl)-piperidin-4-yl]-benzenesulfonamide,
(+/−)-4-methoxy-N-phenyl-N-[cis-1-(2-phenyl-cyclohexyl)-piperidin-4-yl]-benzenesulfonamide,
(+/−)-N-(4-fluoro-phenyl)-4-methyl-N-[cis-1-(2-phenyl-cyclohexyl)-piperidin-4-yl]-benzenesulfonamide,
(+/−)-N-(4-fluoro-phenyl)-4-methoxy-N-[cis-1-(2-phenyl-cyclohexyl)-piperidin-4-yl]-benzenesulfonamide,
(+/−)-4-methoxy-N-[cis-1-(2-phenyl-cyclohexyl)-piperidin-4-yl]-N-(3-trifluoromethyl-phenyl)-benzenesulfonamide and
(+)-4-methoxy-N-phenyl-N-[cis-1-(2-phenyl-cyclohexyl)-piperidin-4-yl]-benzenesulfonamide.

8. A compound according to claim 4, wherein R³ is phenyl, unsubstituted or substituted by chlorine, fluorine, or methyl.

9. A compound according to claim 8, wherein R⁴ is hydroxy.

10. A compound according to claim 8, selected from the group consisting of
(+/−)-N-[cis-1-(2-hydroxy-2-phenyl-cyclohexyl)-piperidin-4-yl]-4-methoxy-N-phenyl-benzenesulfonamide,
(+)-N-[cis-1-(2-hydroxy-2-phenyl-cyclohexyl)-piperidin-4-yl]-4-methoxy-N-phenyl-benzenesulfonamide,
(+/−)-N-(4-chloro-phenyl)-N-[cis-1-(2-hydroxy-2-phenyl-cyclohexyl)-piperidin-4-yl]-4-methoxy-benzenesulfonamide,
(+/−)-N-{cis-1-[2-(4-chloro-phenyl)-2-hydroxy-cyclohexyl]-piperidin-4-yl}-4-methoxy-N-phenyl-benzenesulfonamide,
(+/−)-N-{cis-1-[2-(4-fluoro-phenyl)-2-hydroxy-cyclohexyl]-piperidin-4-yl}-4-methoxy-N-phenyl-benzenesulfonamide,
(+/−)-N-[cis-1-(2-hydroxy-2-o-tolyl-cyclohexyl)-piperidin-4-yl]-4-methoxy-N-phenyl-benzenesulfonamide,
(+/−)-N-(4-fluoro-phenyl)-N-[cis-1-(2-hydroxy-2-phenyl-cyclohexyl)-piperidin-4-yl]-4-methoxy-benzenesulfonamide,
(+/−)-N-(4-fluoro-phenyl)-N-{cis-1-[2-(4-fluoro-phenyl)-2-hydroxy-cyclohexyl]-piperidin-4-yl}-4-methoxy-benzenesulfonamide,
(+/−)-N-[cis-1-(2-hydroxy-2-phenyl-cyclohexyl)-piperidin-4-yl]-4-methoxy-N-(3-methoxy-phenyl)-benzenesulfonamide,
(+/−)-N-{cis-1-[2-(4-fluoro-phenyl)-2-hydroxy-cyclohexyl]-piperidin-4-yl}-4-methoxy-N-(3-methoxy-phenyl)-benzenesulfonamide and
(+/−)-N-[trans-1-(2-hydroxy-2-phenyl-cyclohexyl)-piperidin-4-yl]-4-methoxy-N-phenyl-benzenesulfonamide.

11. A compound according to claim 1, wherein A is —C(O)—.

12. A compound according to claim 11, wherein R⁴ is hydrogen.

13. A compound according to claim 11, wherein R³ is phenyl, unsubstituted or substituted by halogen or lower alkyl.

14. A compound according to claim 13, wherein R³ is unsubstituted phenyl.

15. A compound according to claim 14, wherein R⁴ is hydrogen.

16. A compound according to claim 15, selected from the group consisting of
(+/−)-3-methoxy-N-[cis-1-(2-phenyl-cyclohexyl)-piperidin-4-yl]-N-p-tolyl-benzamide,
(+/−)-4-fluoro-N-[cis-1-(2-phenyl-cyclohexyl)-piperidin-4-yl]-N-p-tolyl-benzamide,
(+/−)-N-(4-chloro-phenyl)-N-[cis-1-(2-phenyl-cyclohexyl)-piperidin-4-yl]-3-trifluoromethyl-benzamide and
(+/−)-N-(4-chloro-phenyl)-3-methoxy-N-[cis-1-(2-phenyl-cyclohexyl)-piperidin-4-yl]-benzamide.

17. A compound according to claim 14 wherein R⁴ is hydroxy.

18. A compound according to claim 17, selected from the group consisting of
(+/−)-N-(4-fluoro-phenyl)-N-[cis-1-(2-hydroxy-2-phenyl-cyclohexyl)-piperidin-4-yl]-3-methoxy-benzamide,
(+/−)-N-(4-chloro-phenyl)-N-[cis-1-(2-hydroxy-2-phenyl-cyclohexyl)-piperidin-4-yl]-3-methoxy-benzamide,
(+/−)-4-fluoro-N-[cis-1-(2-hydroxy-2-phenyl-cyclohexyl)-piperidin-4-yl]-N-p-tolyl-benzamide,
(+/−)-N-[cis-1-(2-hydroxy-2-phenyl-cyclohexyl)-piperidin-4-yl]-N-(3-methoxy-phenyl)-benzamide and
(+/−)-N-[cis-1-(2-hydroxy-2-phenyl-cyclohexyl)-piperidin-4-yl]-3-methoxy-N-p-tolyl-benzamide.

19. A compound according to claim 3, wherein R¹ is phenyl, unsubstituted or substituted by one or two substituents selected from the group consisting of lower alkyl, lower alkoxy, —OCF₃, halogen, —NR'R" and trifluoromethyl.

20. A compound according to claim 3, wherein R² is phenyl, unsubstituted or substituted by one or two substituents selected from the group consisting of lower alkyl, lower alkoxy, halogen, trifluoromethyl, nitro, cyano, —NR'R", and hydroxy.

21. A compound according to claim 11, wherein R¹ is phenyl, unsubstituted or substituted by one or two substituents selected from the group consisting of lower alkyl, lower alkoxy, —OCF₃, halogen, —NR'R" and trifluoromethyl.

22. A compound according to claim 11, wherein R² is phenyl, unsubstituted or substituted by one or two substituents selected from the group consisting of lower alkyl, lower alkoxy, halogen, trifluoromethyl, nitro, cyano, —NR'R", and hydroxy.

23. A compound according to claim 1, wherein R³ is phenyl, unsubstituted or substituted by halogen or lower alkyl.

24. A composition comprising a compound of formula I

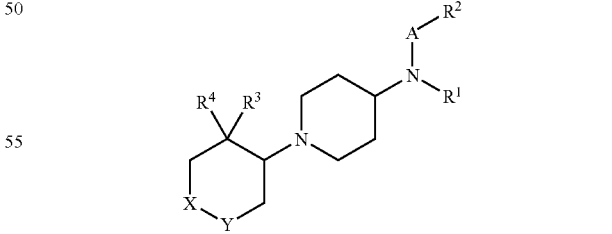

wherein
R¹ is lower alkyl, —(CH₂)ₙ-aryl, unsubstituted or substituted by one or two substituents selected from the group consisting of lower alkyl, lower alkoxy, —OCF₃, halogen, —NR'R" and trifluoromethyl;
R² is lower alkyl, —(CH₂)ₙ-aryl, unsubstituted or substituted by one or two substituents selected from the group consisting of lower alkyl, lower alkoxy, halogen, trifluoromethyl, nitro, cyano, —NR'R", and hydroxy;

$R^3$ is aryl, unsubstituted or substituted by halogen or lower alkyl;
$R^4$ is hydrogen or hydroxy;
A is —S(O)$_2$— or —C(O)—;
X and Y are each —CH$_2$—;
R' and R" are each independently selected from the group consisting of hydrogen, lower alkyl and —C(O)-lower alkyl;
n is 0, 1 or 2;
or a pharmaceutically acceptable acid addition salt thereof and a pharmaceutically acceptable carrier.

25. A process for preparation of a compound of formula I in accordance with claim 1, which process comprises reacting a compound of formula

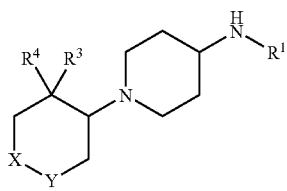

with a compound of formula

in the presence of a base and/or a proton scavenger to produce a compound of formula

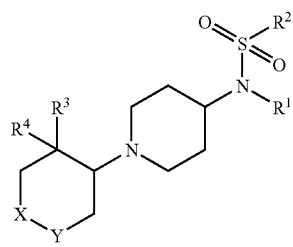

wherein X, Y, $R^1$, $R^2$ and $R^3$ are as defined in claim 1.

26. A process for preparation of a compound of formula I in accordance with claim 1, which process comprises reacting a compound of formula

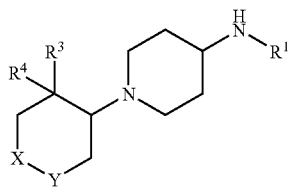

with a compound of formula

in the presence of a base and/or a proton scavenger to produce a compound of formula

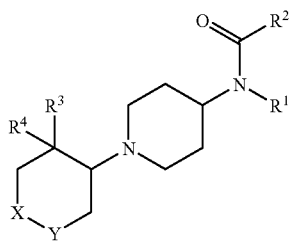

wherein X, Y, $R^1$, $R^2$ and $R^3$ are as defined in claim 1.

27. A process for preparation of a compound of formula I in accordance with claim 1, which process comprises reacting a compound of formula

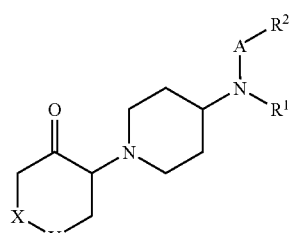

with a compound of formula

to produce a compound of formula

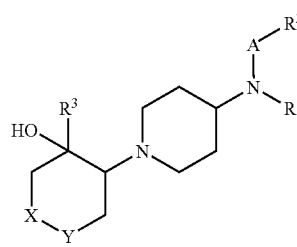

wherein A, X, Y, $R^1$, $R^2$ and $R^3$ are as defined in claim 1.

28. A process for preparation of a compound of formula I in accordance with claim 1, which process comprises reacting a compound of formula

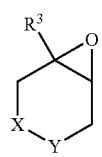

with a compound of formula

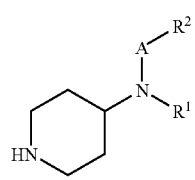

to produce a compound of formula

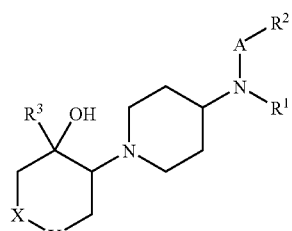

wherein A, X, Y, $R^1$, $R^2$ and $R^3$ are as defined in claim 1.

* * * * *